(12) United States Patent
Wolf et al.

(10) Patent No.: US 7,109,250 B2
(45) Date of Patent: Sep. 19, 2006

(54) MULTIMER FORMS OF ACYLPHOSPHINES AND THEIR DERIVATIVES

(75) Inventors: Jean-Pierre Wolf, Maisprach (CH); Gebhard Hug, Rheinfelden (CH)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 78 days.

(21) Appl. No.: 10/495,958

(22) PCT Filed: Nov. 13, 2002

(86) PCT No.: PCT/EP02/12680

§ 371 (c)(1),
(2), (4) Date: May 17, 2004

(87) PCT Pub. No.: WO03/044030

PCT Pub. Date: May 30, 2003

(65) Prior Publication Data

US 2005/0004247 A1 Jan. 6, 2005

(30) Foreign Application Priority Data

Nov. 20, 2001 (EP) .................................. 01811113

(51) Int. Cl.
- C08F 2/50 (2006.01)
- G03F 7/029 (2006.01)
- C07F 9/53 (2006.01)
- C07F 9/58 (2006.01)
- C03C 25/10 (2006.01)

(52) U.S. Cl. ..................... 522/18; 522/26; 522/28; 522/29; 522/64; 568/14; 568/15

(58) Field of Classification Search ............... 522/64, 522/18, 28, 29, 26; 568/15, 14
See application file for complete search history.

(56) References Cited

U.S. PATENT DOCUMENTS

| | | | | |
|---|---|---|---|---|
| 4,265,723 A * | 5/1981 | Hesse et al. | .................. | 522/16 |
| 4,522,693 A * | 6/1985 | Henne et al. | .................. | 522/27 |
| 5,218,009 A | 6/1993 | Rutsch et al. | .................. | 522/16 |
| 5,723,512 A | 3/1998 | Leppard et al. | ................. | 522/55 |
| 6,075,065 A * | 6/2000 | Yamazaki et al. | ............. | 522/64 |
| 6,136,880 A * | 10/2000 | Snowwhite et al. | ........ | 522/364 |
| 6,399,805 B1 * | 6/2002 | Wolf et al. | .................. | 556/405 |
| 6,579,663 B1 * | 6/2003 | Wolf et al. | .................. | 430/281.1 |
| 6,737,549 B1 | 5/2004 | Wolf et al. | .................. | 568/14 |
| 6,979,733 B1 * | 12/2005 | Zhao et al. | ................. | 536/23.2 |
| 2001/0031898 A1 | 10/2001 | Wolf et al. | .................. | 568/13 |

FOREIGN PATENT DOCUMENTS

| | | |
|---|---|---|
| DE | 19618720 | 11/1996 |
| DE | 10105046 | 8/2001 |
| EP | 0413657 | 2/1991 |
| EP | 0670323 | 9/1995 |
| JP | 2001 200007 | 7/2001 |

OTHER PUBLICATIONS

Derwent Abstract 97-044005/05 for DE 19618720 (1996).

* cited by examiner

*Primary Examiner*—Susan Berman
(74) *Attorney, Agent, or Firm*—Tyler A. Stevenson

(57) ABSTRACT

Compounds of the formula (I), in which E is O or S; and x is 0 or 1, A is cyclopentyl, cyclohexyl, naphthyl, biphenylyl, anthracyl or an O-, S- or N-containing 5- or 6-membered heterocyclic ring, where the mentioned radicals are unsubstituted or substituted by halogen, $C_1$–$C_4$alkyl or $C_1$–$C_4$alkoxy; or A is a group formula (II) R is $C_1$–$C_{24}$alkyl, unsubstituted or substituted, $C_2$–$C_{24}$alkyl which is interrupted once or more than once by nonconsecutive O, S or $NR_{14}$ and which is unsubstituted or substituted, $C_2$–$C_{24}$alkenyl which is uninterrupted or interrupted once or more than once by nonconsecutive O, S or $NR_{14}$ and which is unsubstituted or substituted, $C_5$–$C_{24}$cycloalkenyl which is uninterrupted or interrupted once or more than once by nonconsecutive O, S or $NR_{14}$ and which is unsubstituted or substituted; $C_7$–$C_{24}$arylalkyl which is unsubstituted or substituted on the aryl group. $C_4$–$C_{24}$cycloalkyl which is uninterrupted or interrupted once or more then once by O, S or $NR_{14}$ and which is unsubstituted or substituted, $C_8$–$C_{24}$arylcycloalkyl or $C_8$–$C_{24}$arylcycloalkenyl; or, R is a group of the formula (III) W is a bond, —CO—O— or —CO—N($R_{15}$)—; L a di-tri-or tetravalent linking group, n is a number of 2,3 or 4;

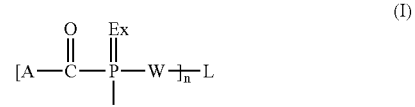

(I)

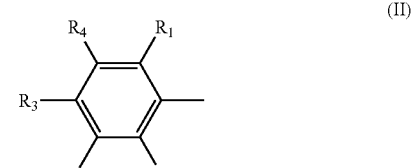

(II)

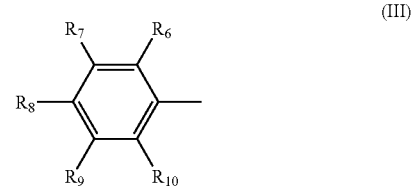

(III)

9 Claims, No Drawings

MULTIMER FORMS OF ACYLPHOSPHINES AND THEIR DERIVATIVES

The present application relates to dimer and multimer forms of acylphosphines, acylphosphine oxides and acylphosphinesulfides to the preparation thereof, and to the use thereof as photoinitiators.

E. Lindner et al describe in Z. Naturforschung, B: Anorg. Chem., Org. Chem. (1978), 33B(12), 1457–60 dimer forms of acylphosphine oxides as for example 1,2-ethanediylbis-benzoylphenylphosphine oxides with respect of their behavior towards molecular oxygen.

The German Patent Publication DE19618720 describes bisacyl-bisphosphine oxides as for example 1,2-bis(2,4-di-pentoxyphenyl)-1,2bis(2,4,6-trimethylbenzyol)diphosphine oxide being useful in photopolymerisable compositions.

It has now been found that dimer and multimer forms of acylphosphines, acylphosphine oxides and acylphosphinesulfides as described below show an improved curing behaviour due to additional crosslinking and furthermore, contain less volatile decomposition products and by products than known acyl- and bis-acylphosphine oxides.

The invention provides compounds of the formula I

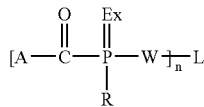

(I), in which

E is O or S and x is 0 or 1,

A is cyclopentyl, cyclohexyl, naphthyl, biphenylyl, anthracyl or an O-, S- or N-containing 5- or 6-membered heterocyclic ring, where the radicals cyclopentyl, cyclohexyl, naphthyl, biphenylyl, anthracyl or O—, S— or N-containing 5- or 6-membered heterocyclic ring are unsubstituted or substituted by halogen, $C_1$–$C_4$alkyl or $C_1$–$C_4$alkoxy; or A is a group

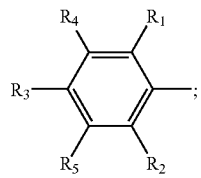

wherein $R_1$ and $R_2$ independently of one another are $C_1$–$C_{24}$alkyl, $OR_{11}$, $CF_3$ or halogen;

$R_3$, $R_4$ and $R_5$ independently of one another are hydrogen, $C_1$–$C_{24}$alkyl, $OR_{11}$ or halogen; or two of the radicals $R_1$, $R_2$, $R_3$, $R_4$ or $R_5$ together form $C_2$–$C_{12}$alkylene, which can be interrupted by O, S or $NR_{14}$;

R is $C_1$–$C_{24}$alkyl, unsubstituted or substituted by $C_3$–$C_{24}$cycloalkyl, $C_3$–$C_{24}$cycloalkenyl, phenyl, CN, $C(O)R_{11}$, $C(O)OR_{11}$, $C(O)N(R_{14})_2$, $OC(O)R_{11}$, $OC(O)OR_{11}$, $N(R_{14})C(O)N(R_{14})$, $OC(O)NR_{14}$, $N(R_{14})C(O)OR_{11}$, halogen, $OR_{11}$, $SR_{11}$ or $N(R_{12})(R_{13})$;

$C_2$–$C_{24}$alkyl which is interrupted once or more than once by nonconsecutive O, S or $NR_{14}$ and which is unsubstituted or substituted by phenyl, $OR_{11}$, $SR_{11}$, $N(R_{12})(R_{13})$, CN, $C(O)R_{11}$, $C(O)OR_{11}$, or $C(O)N(R_{14})_2$;

$C_2$–$C_{24}$alkenyl which is uninterrupted or interrupted once or more than once by nonconsecutive O, S or $NR_{14}$ and which is unsubstituted or substituted by $OR_{11}$, $SR_{11}$, $N(R_{12})(R_{13})$, or $C_1$–$C_{12}$alkyl;

$C_5$–$C_{24}$cycloalkenyl which is uninterrupted or interrupted once or more than once by nonconsecutive O, S or $NR_{14}$ and which is unsubstituted or substituted by $OR_{11}$, $SR_{11}$, $N(R_{12})(R_{13})$, or $C_1$–$C_{12}$alkyl;

$C_7$–$C_{24}$arylalkyl which is unsubstituted or substituted on the aryl group by $C_1$–$C_{12}$alkyl, $C_1$–$C_{12}$alkoxy or halogen;

$C_4$–$C_{24}$cycloalkyl which is uninterrupted or interrupted once or more than once by O, S or $NR_{14}$ and which is unsubstituted or substituted by $OR_{11}$, $SR_{11}$, $N(R_{12})(R_{13})$, or $C_1$–$C_{12}$alkyl;

$C_8$–$C_{24}$arylcycloalkyl or $C_8$–$C_{24}$arylcycloalkenyl; or;

R is a group of the formula

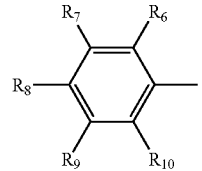

wherein $R_6$, $R_7$, $R_8$, $R_9$ and $R_{10}$ independently of one another are hydrogen, $C_1$–$C_{24}$alkyl;

$C_2$–$C_{24}$alkyl which is interrupted once or more than once by nonconsecutive O, S or $NR_{14}$ and which is unsubstituted or substituted by OH, SH; $SR_{11}$ or $N(R_{12})(R_{13})$, $OR_{11}$, phenyl or halogen;

W is a bond, —CO—O— or —CO—N($R_{15}$)—;

L is a di-tri-or tetravalent linking group, n is a number of 2,3 or 4;

$R_{11}$ is hydrogen, $C_1$–$C_{20}$alkyl, $C_2$–$C_{20}$alkenyl, $C_3$–$C_8$cycloalkyl, phenyl unsubstituted or substituted by one or more $C_1$–$C_4$alkyl, benzyl or $C_2$–$C_{20}$alkyl which is interrupted once or more than once by O or S and which is unsubstituted or is substituted by OH or SH;

$R_{12}$ and $R_{13}$ independently of one another are hydrogen, $C_1$–$C_{20}$alkyl, $C_3$–$C_8$cycloalkyl, phenyl unsubstituted or substituted by one or more $C_1$–$C_4$alkyl, benzyl or $C_2$–$C_{20}$alkyl which is interrupted once or more than once by nonconsecutive O atoms and which is unsubstituted or substituted by OH or SH; or $R_{12}$ and $R_{13}$ together are $C_3$–$C_5$alkylene which is uninterrupted or interrupted by O, S or $NR_{14}$;

$R_{14}$ is hydrogen, phenyl unsubstituted or substituted by one or more $C_1$–$C_4$alkyl, $C_1$–$C_{12}$alkyl or $C_2$–$C_{12}$alkyl which is interrupted once or more than once by nonconsecutive O or S atoms and which is unsubstituted or substituted by OH or SH;

$R_{15}$ is hydrogen, $C_1$–$C_{20}$alkyl, phenyl unsubstituted or substituted once or more with $C_1$–$C_4$alkyl.

General Definitions

As used herein, the term "$C_1$–$C_{24}$alkyl" refers to straight and branched aliphatic hydrocarbon chains, for example, $C_1$–$C_{24}$alkyl, $C_1$–$C_{20}$alkyl, $C_1$–$C_{18}$alkyl, $C_1$–$C_{12}$alkyl, $C_1$–$C_8$alkyl, $C_1$–$C_6$alkyl or $C_1$–$C_4$alkyl. Specific examples are: methyl, ethyl, n-propyl, isopropyl, n-butyl, sec-butyl, tert-butyl, pentyl, isoamyl, n-hexyl, heptyl, 2,4,4-trimethylpentyl, 2-ethylhexyl, octyl, nonyl, decyl, undecyl, dodecyl, tetradecyl, pentadecyl, hexadecyl, heptadecyl, octadecyl, nonadecyl, icosyl or tetraicosyl. $C_2$–$C_{24}$alkyl which is interrupted once or more than once by O, S or $NR_{14}$ is, for example, interrupted 1–9 times, e.g. 1–7 times or once or twice, by O, S or $NR_{14}$. It the radicals are interrupted by two or more O, S or $NR_{14}$, then the O atoms, S atoms or $NR_{14}$ groups are in each case separated from one another by at least one methylene group. The O atoms, S atoms or $NR_{14}$ groups are thus not directly consecutive. The alkyl radical can be linear or branched. For example, structural units such as —$CH_2$—O—$CH_3$, —$CH_2CH_2$—O—$CH_2CH_3$, —[$CH_2CH_2O$]$_z$—$CH_3$, where z=1 to 9, —($CH_2CH_2O$)$_7$$CH_2CH_3$, —$CH_2$—$CH(CH_3)$—O—$CH_2$—$CH_2CH_3$, —$CH_2$—$CH(CH_3)$—O—$CH_2$—$CH_3$, —$CH_2SCH_3$ or —$CH_2$—$N(CH_3)_2$ arise.

As used herein, the term "$C_2$–$C_{24}$Alkenyl" refers to radicals which are mono- or polyunsaturated, and are linear or branched and are, for example, $C_2$–$C_{18}$alkenyl, $C_2$–$C_8$alkenyl, $C_2$–$C_6$alkenyl or $C_2$–$C_4$alkenyl. Examples are vinyl, allyl, methallyl, 1,1-dimethylallyl, 1-butenyl, 2-butenyl, 1,3-pentadienyl, 1-hexenyl, 1-octenyl, decenyl or dodecenyl, in particular allyl. $C_2$–$C_{18}$Alkenyl has the same meanings as given above apart from the corresponding number of carbon atoms. If $C_2$–$C_{24}$alkenyl radicals are interrupted, for example, by O, then the following structures are, for example, included: —($CH_2$)$_y$—O—($CH_2$)$_x$—CH=$CH_2$, —($CH_2$)$_y$—O—($CH_2$)$_x$—$C(CH_3)$=$CH_2$ or —($CH_2$)$_y$O—CH=$CH_2$, where x and y independently of one another are a number from 1 to 21.

As used herein, the term "$C_1$–$C_{24}$Alkylene" refers to linear or branched and is, for example, $C_1$–$C_{20}$alkylene, $C_1$–$C_{12}$alkylene, $C_1$–$C_8$alkylene, $C_2$–$C_8$alkylene, $C_1$–$C_4$alkylene, for example methylene, ethylene, propylene, isopropylene, n-butylene, sec-butylene, isobutylene, tert-butylene, pentylene, hexylene, heptylene, octylene, nonylene, decylene, dodecylene, tetradecylene, heptadecylene, octadecylene, icosylene or e.g. $C_1$–$C_{12}$alkylene, for example ethylene, decylene,

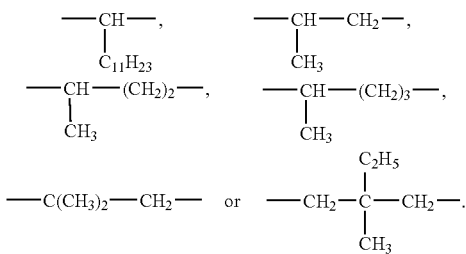

$C_2$–$C_{18}$Alkylene is also linear or branched, e.g. $C_2$–$C_8$alkylene or $C_2$–$C_4$alkylene and has the meanings given above apart from the corresponding number of carbon atoms. If $C_2$–$C_{24}$alkylene is interrupted once or more than once by O, S or $NR_{14}$, then it is, for example, interrupted 1–9 times, e.g. 1–7 times or once or twice by O, S or $NR_{14}$, and, for example, structural units such as —$CH_2$—O—$CH_2$—, —$CH_2CH_2$—O—$CH_2CH_2$—, —[$CH_2CH_2O$]$_z$—, where z=1 to 9, —($CH_2CH_2O$)$_7$$CH_2CH_2$—, —$CH_2$—$CH(CH_3)$—O—$CH_2$—$CH(CH_3)$—, —$CH_2$—S—$CH_2$—, —$CH_2CH_2$—S—$CH_2CH_2$—, —$CH_2CH_2$—S—$CH_2CH_2CH_2$—, —($CH_2$)$_3$—S—($CH_2$)$_3$—S—($CH_2$)$_3$—, —$CH_2$—($NR_{14}$)—$CH_2$— or —$CH_2CH_2$—($NR_{14}$)—$CH_2CH_2$— arise. The alkylene radicals can be linear or branched and, if the alkylene radicals are interrupted by two or more O, S or $NR_{14}$ groups, then the O, S and $NR_{14}$ are not consecutive, but in each case are separated from one another by at least one methylene group.

As used herein, the term "$C_2$–$C_{24}$Alkenylene" refers to mono- or polyunsaturated and linear or branched and e.g. $C_2$–$C_{18}$alkenylene or $C_2$–$C_8$alkenylene. Examples are ethenylene, propenylene, butenylene, pentenylene, hexenylene, octenylene, e.g. 1-propenylene, 1-butenylene, 3-butenylene, 2-butenylene, 1,3-pentadienylene, 5hexenylene or 7-octenylene. If $C_2$–$C_{24}$Alkenylene is interrupted once or more than once by O, S, $NR_{14}$, then it is mono- or polyunsaturated and linear or branched and is, for example, interrupted 1–9 times, e.g. 1–7 times or once or twice, by O, S or $NR_{14}$, where in the case of two or more O, S or $NR_{14}$, these are in each case separated from one another by at least one methylene group. Here, the meanings for $C_2$–$C_{24}$alkenylene are as defined above.

As used herein, the term "$C_3$–$C_{24}$cycloalkyl, e.g. $C_5$–$C_{12}$cycloalkyl, $C_3$–$C_{12}$cycloalkyl, $C_3$–$C_8$cycloalkyl, stands both for individual alkyl ring systems and also bridged alkyl ring systems. Furthermore, the radicals can also contain linear or branched alkyl groups (as described above apart from the corresponding number of carbon atoms). Examples are cyclopropyl, cyclopentyl, cyclohexyl, cyclooctyl, cyclododecyl, cycloicosyl, adamantyl, in particular cyclopentyl and cyclohexyl, preferably cyclohexyl.

Further examples are

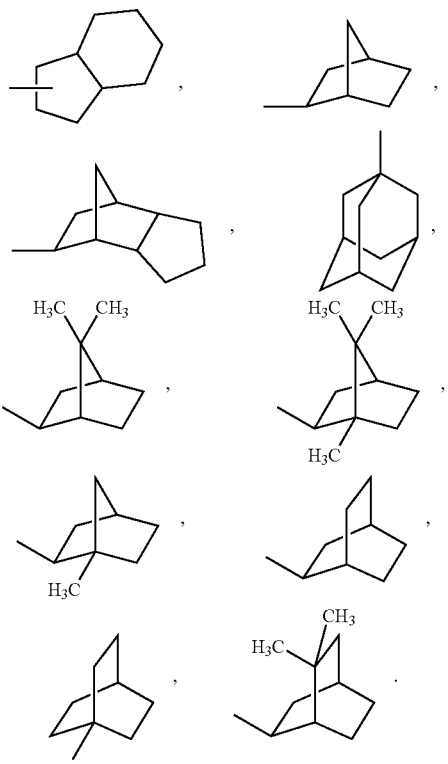

$C_3$–$C_8$cycloalkyl, e.g. $C_3$–$C_6$cycloalkyl, can have the meaning given about apart form the corresponding number of carbon atoms.

$C_3$–$C_{18}$cycloalkyl substituted by $C_1$–$C_{20}$alkyl, $OR_{11}$, $CF_3$ or halogen is preferably tri- or disubstituted in the 2,4,6- or 2,6-positions respectively, of the cycloalkyl ring. Preference is given to 2,4,6-trimethylcyclohexyl and 2,6-dimethoxycyclohexyl. The cycloalkyl group may be interrupted 1–9 times, e.g. 1–7 times or once or twice, by O, S or $NR_{14}$, where in the case of two or more O, S or $NR_{14}$, these are in each case separated from one another by at least one methylene group As used herein, the term "$C_3$–$C_{24}$Cycloalkenyl", e.g. $C_5$–$C_{12}$cycloalkenyl, $C_3$–$C_{12}$cycloalkenyl, $C_3$–$C_8$cycloalkenyl, stands both for individual alkyl ring systems and also bridged alkyl ring systems and can be mono- or polyunsaturated, e.g. mono- or diunsaturated. Furthermore, the radicals can also contain linear or branched alkyl groups (as described above apart from the corresponding number of carbon atoms). Examples are cyclopropenyl, cyclopentenyl, cyclohexenyl, cyclooctenyl, cyclododecenyl, cycloicosenyl, in particular cyclopentenyl and cyclohexenyl, preferably cyclohexenyl. The cycloalkenyl group may be interrupted 1–9 times, e.g. 1–7 times or once or twice, by O, S or $NR_{14}$, where in the case of two or more O, S or $NR_{14}$, these are in each case separated from one another by at least one methylene group As used herein, the term "$C_4$–$C_{18}$Cycloalkylene" is linear or branched and can be either an individual ring or bridged alkyl rings, for example adamantyl. It is e.g. $C_4$–$C_{12}$cycloalkylene or $C_4$–$C_8$cycloalkylene, for example cyclopentylene, cyclohexylene, cyclooctylene, cyclododecylene, in particular cyclopentylene and cyclohexylene, preferably cyclohexylene. However, $C_4$–$C_{18}$cycloalkylene likewise stands for structural units such as

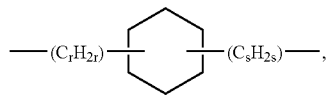

in which r and s independently of one another are 0–12 and the sum r+s is $\leq 12$, or

in which r and s independently of one another are 0-13 and the sum r+s is —13. $C_4$–$C_{18}$cycloalkylene interrupted once or more than once by O, S or $NR_{14}$ stands for cycloalkylene units as described above which can be interrupted either in the ring unit or in the side-chain unit e.g. 1–9 times, 1–7 times or once or twice, by O, S or $NR_{14}$.

As used herein, the term "$C_3$–$C_{24}$Cycloalkenylene" is linear or branched and can be either an individual ring or bridged rings and is mono- or polyunsaturated. It is e.g. $C_3$–$C_{12}$cycloalkenylene or $C_3$–$C_8$cycloalkenylene, for example cyclopentenylene, cyclohexenylene, cyclooctenylene, cyclododecenylene, in particular cyclopentenylene and cyclohexenylene, preferably cyclohexenylene. $C_3$–$C_{24}$Cycloalkenylene also, however, stands for structural units such as

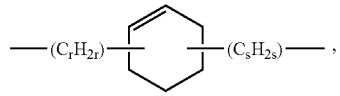

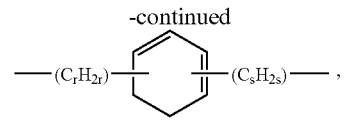

in which r and s independently of another are 0–12 and the sum r+s is $\leq 12$, or

or

in which r and s independently of one another are 0–13 and the sum r+s is $\leq 13$. $C_3$–$C_{24}$Cycloalkenylene interrupted once or more than once by O, S or $NR_{14}$ stands for cycloalkenylene units as described above which can be interrupted either in the ring unit or in the side-chain unit e.g. 1–9 times, 1–7 times or once or twice by O, S or $NR_{14}$. Examples are

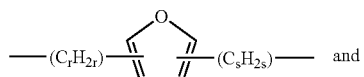 and

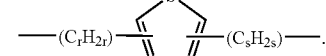

Halogen is fluorine, chlorine, bromine or iodine, in particular fluorine, chlorine and bromine, preferably chlorine. $R_1$, $R_1'$, $R_2$, $R_2'$, $R_3$ and $R_3'$ as halogen are, in particular, chlorine.

As used herein, the term aryl is, for example, phenyl, naphthyl, biphenyl, anthracyl or phenanthryl.

As used herein, the term $C_7$–$C_{24}$Arylalkyl is, for example, $C_7$–$C_{16}$arylalkyl, $C_7$–$C_{11}$arylalkyl. The alkyl radical in this group can either be linear or branched. Examples are benzyl, phenylethyl, α-methylbenzyl, phenylpentyl, phenylhexyl, α,α-dimethylbenzyl, naphthylmethyl, naphthylethyl, naphthyleth-1-yl or naphthyl-1-methyl-eth-1-yl, in particular benzyl. Substituted $C_7$–$C_{24}$arylalkyl is substituted one to four times, e.g. once, twice or three times, in particular once or twice, on the aryl ring.

As used herein, the term $C_8$–$C_{24}$Arylcycloalkyl is e.g. $C_9$–$C_{16}$arylcycloalkyl, $C_9$–$C_{13}$arylcycloalkyl and is cycloalkyl which is fused with one or more aryl rings. Examples are

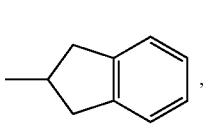 , 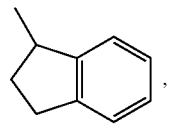 ,

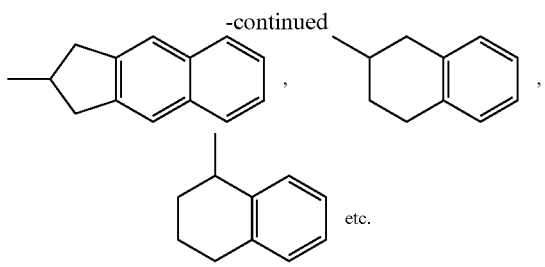 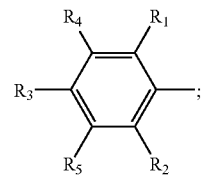

Specific Definitions:

Concerning the Residue A

The term "heterocyclic ring", as used herein, refers to e.g. furyl, thienyl, pyrrolyl, oxinyl, dioxinyl or pyridyl. Said heterocyclic radicals can be mono- or polysubstituted, e.g. mono-substituted or disubstituted, by halogen, linear or branched $C_1$–$C_4$alkyl, such as methyl, ethyl, propyl, butyl, or $C_1$–$C_4$alkoxy. Examples thereof are dimethylpyridyl, dimethylpyrrolyl or methylluryl.

A is, for example, 2-methylnaphth-2-yl, 2-methoxynaphth-2-yl, 1,3-dimethylnaphth-2-yl, 2,8-dimethylnaphth-1-yl, 1,3-dimethoxynaphth-2-yl, 1,3-dichloronaphth-2-yl, 2,8-dimethoxynaphth-1-yl, 2,4,6-trimethylpyrid-3-yl, 2,4-dimethoxyfuran-3-yl or 2,4,5-trimethylthien-3-yl.

Preference is given to compounds of the formula I in which A is a radical

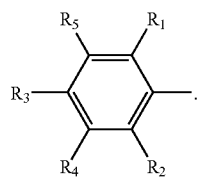

If case that two of the radicals $R_1$, $R_2$, $R_3$, $R_4$ or $R_5$ form $C_2$–$C_{12}$alkylene, then, for example, the following structures arise

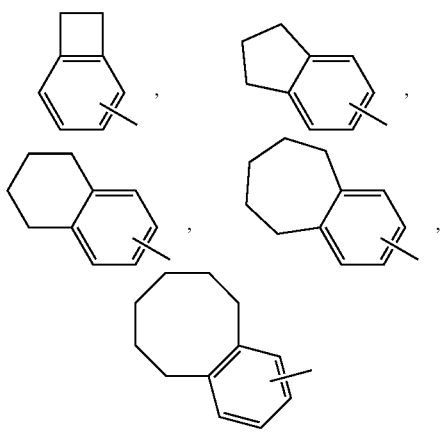

The alkylene chain may be interrupted by —O—, —S— or —$NR_{14}$.

Preferred are compounds of the formula I in which A is a group

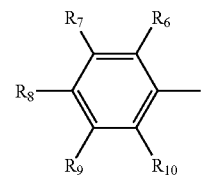

wherein
$R_1$ and $R_2$ independently of one another are $C_1$–$C_{12}$alkyl, $OR_{11}$, $CF_3$ or halogen; more preferably $C_1$–$C_4$alkyl, $C_1$–$C_4$alkoxy, $CF_3$ or Cl;
$R_3$, $R_4$ and $R_5$ independently of one another are hydrogen, $C_1$–$C_{12}$alkyl, $OR_{11}$ or halogen; more preferably hydrogen, $C_1$–$C_4$alkyl, $C_1$–$C_4$alkoxy or Cl.

The residue R, may be an aliphatic or an aromatic residue. The aliphatic residue R is preferably
$C_1$–$C_{12}$alkyl, unsubstituted or substituted by phenyl, CN, $OR_{11}$, $C(O)R_{11}$, $C(O)OR_{11}$, $C(O)N(R_{14})_2$;
$C_2$–$C_{12}$alkyl which is interrupted once or more than once by nonconsecutive O and which is unsubstituted or substituted by phenyl, CN, $OR_{11}$, $C(O)R_{11}$, $C(O)OR_{11}$, $C(O)N(R_{14})_2$;
$C_2$–$C_{12}$alkenyl which is uninterrupted or interrupted once or more than once by nonconsecutive O and which is unsubstituted or substituted by $OR_{11}$, $N(R_{12})(R_{13})$, or $C_1$–$C_{12}$alkyl;
benzyl;
$C_4$–$C_8$cycloalkyl which is uninterrupted or interrupted once or more than once by O, S or $NR_{14}$ and which is unsubstituted or substituted by $OR_{11}$, $SR_{11}$, $N(R_{12})(R_{13})$, or $C_1$–$C_{12}$alkyl;
$C_8$–$C_{12}$arylcycloalkyl; whereby
$R_{11}$ is hydrogen, $C_1$–$C_{12}$alkyl, $C_5$–$C_6$cycloalkyl, phenyl or benzyl;
$R_{12}$ and $R_{13}$ independently of one another are hydrogen, $C_1$–$C_{12}$alkyl, phenyl, benzyl or $C_2$–$C_{12}$alkyl which is interrupted once or more than once by nonconsecutive O atoms and which is unsubstituted or substituted by OH or SH; or $R_{12}$ and $R_{13}$ together are piperidino, morpholino or piperazino;;
$R_{14}$ is hydrogen, phenyl, $C_1$–$C_{12}$alkyl or $C_2$–$C_{12}$alkyl which is interrupted once or more than once by nonconsecutive O atoms and which is unsubstituted or substituted by OH or SH;

Most preferably the aliphatic residue R is $C_1$–$C_{12}$alkyl.
The aromatic residue R is preferably a group of the formula wherein
$R_6$, $R_7$, $R_8$, $R_9$ and $R_{10}$ independently of one another are hydrogen, $C_1$–$C_{12}$alkyl, $OR_{11}$, phenyl or halogen; more preferably $C_1$–$C_4$alkyl; $C_1$–$C_4$alkoxy, phenyl or Cl.

The divalent linking group is selected from arylene, linear or branched $C_2$–$C_{24}$alkylene which is unsubstituted or substituted once or more than once by $C_1$–$C_{20}$alkyl, $C_1$–$C_{20}$alkoxy, —S—$C_1$–$C_{20}$alkyl, phenoxy, —O-aryl, —O—CO-aryl, O—CO—$C_1$–$C_{20}$alkyl, —N—(CO—$C_1$–$C_{20}$alkyl)$_2$, —CO—N—($C_1$–$C_{20}$alkyl)$_2$, —COO—$C_1$–$C_{20}$alkyl, —COO-aryl, CN, $CF_3$, F, $CH_2Cl$, $CH_2Br$, linear or branched $C_2$–$C_{24}$alkylene which is interrupted once or more than once by non-consecutive —O—, —S— atoms or by groups selected from —N($R_{16}$)—, —CO—N($R_{16}$)—, —CO—, —O—CO—, —CO—O—, —O—COO—, phenylene, arylene, cycloalkylene, —CH=CH—, bicycloalkylene, biphenylene, —Si($CH_3$)$_2$—, —Si($CH_3$)$_2$—O—Si($CH_3$)$_2$—, —Si($CH_3$)$_2$—O-phenylene-O—Si($CH_3$)$_2$—, —$CF_2$— or 2,2-dimethyl-1,3-dioxolane-4,5-diyl, and which is unsubstituted or substituted once or more than once by $C_1$–$C_{20}$alkyl, $C_1$–$C_{20}$alkoxy, —S—$C_1$–$C_{20}$alkyl, phenoxy, —O-aryl, —O—CO-aryl, O—CO—$C_1$–$C_{20}$alkyl, —N—(CO—$C_1$–$C_{20}$alkyl)$_2$, —CO—N—($C_1$–$C_{20}$alkyl)2, —COO—$C_1$–$C_{20}$alkyl, —COO-aryl, CN, $CF_3$, F, $CH_2Cl$, $CH_2Br$; with the proviso, that L is not ethylene.

The group $R_{10}$ is $C_1$–$C_{20}$alkyl, —CO—$C_1$–$C_{20}$alkyl, aryl, —CO-aryl.

The trivalent linking group is selected from linear or branched $C_3$–$C_{24}$alkylene which is unsubstituted or substituted once or more than once by $C_1$–$C_{20}$alkyl, $C_1$–$C_{20}$alkoxy, —S—$C_1$–$C_{20}$alkyl, phenoxy, —O-aryl, —O—CO-aryl, O—CO—$C_1$–$C_{20}$alkyl, —N—(CO—$C_1$–$C_{20}$alkyl)$_2$, —CO—N—($C_1$–$C_{20}$alkyl)$_2$, —COO—$C_1$–$C_{20}$alkyl, —COO-aryl, CN, $CF_3$, F, $CH_2Cl$, $CH_2Br$, linear or branched $C_3$–$C_{24}$alkylene which is interrupted once or more than once by non-consecutive —O—, —S— atoms or by groups selected from —N($R_{18}$)—, —CO—N($R_{16}$)—, —CO—, —O—CO—, —CO—O—, —O—COO—, phenylene, arylene, cycloalkylene, —CH=CH—, bicycloalkylene, biphenylene, —Si($CH_3$)$_2$—, —Si($CH_3$)$_2$—O—Si($CH_3$)$_2$—, —Si($CH_3$)$_2$—O-phenylene-O—Si($CH_3$)$_2$—, —$CF_2$— or 2,2-dimethyl-1,3-dioxolane-4,5-diyl, and which is unsubstituted or substituted once or more than once by $C_{-C20}$alkyl, $C_1$–$C_{20}$alkoxy, —S—$C_1$–$C_{20}$alkyl, phenoxy, —O-aryl, —O—CO-aryl, O—CO—$C_1$–$C_{20}$alkyl, —N—(CO—$C_1$–$C_{20}$alkyl)$_2$, —CO—N—(CO—$C_1$–$C_{20}$alkyl)2, —COO—$C_1$–$C_{20}$alkyl, —COO-aryl, CN, $CF_3$, F, $CH_2Cl$, $CH_2Br$, or the trivalent linking group is selected from —[—($C_1$–$C_{24}$alkyl)-O—]$_3$—P  or  —[—($C_1$–$C_{24}$alkyl)-O—]$_3$—P=O or is a group of the formula

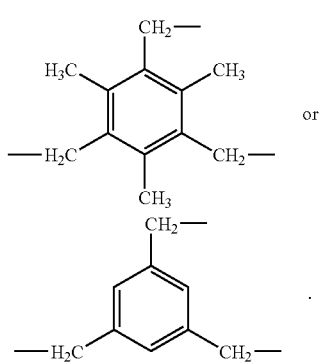

The tetravalent linking group is selected from linear or branched $C_4$–$C_{24}$alkylene which is unsubstituted or substituted once or more than once by $C_1$–$C_{20}$alkyl, $C_1$–$C_{20}$alkoxy, —S—$C_1$–$C_{20}$alkyl, phenoxy, —O-aryl, —O—CO-aryl, O—CO—$C_1$–$C_{20}$alkyl, —N—(CO—$C_1$–$C_{20}$alkyl)$_2$, —CO—N—($C_1$–$C_{20}$alkyl)2, —COO—$C_1$–$C_{20}$alkyl, —COO-aryl, CN, $CF_3$, F, $CH_2Cl$, $CH_2Br$, linear or branched $C_4$–$C_{24}$alkylene which is interrupted once or more than once by non-consecutive —O—, —S— atoms or by groups selected from —N($R_{16}$)—, —CO—N($R_{16}$)—, —CO—, —O—CO—, —CO—O—, —O—COO—, phenylene, arylene, cycloalkylene, —CH=CH—, bicycloalkylene, biphenylene, —Si($CH_3$)$_2$—, —Si($CH_3$)$_2$—O—Si($CH_3$)$_2$—, —Si($CH_3$)$_2$—O-phenylene-O—Si($CH_3$)$_2$—, —$CF_2$— or 2,2-dimethyl-1,3-dioxolane-4,5-diyl, and which is unsubstituted or substituted once or more than once by $C_1$–$C_{20}$alkyl, $C_1$–$C_{20}$alkoxy, —S—$C_1$–$C_{20}$alkyl, phenoxy, —O-aryl, —O—CO-aryl, O—CO—$C_1$–$C_{20}$alkyl, —N—(CO—$C_1$–$C_{20}$alkyl)$_2$, —CO—N—($C_1$–$C_{20}$alkyl)2, —COO—$C_1$–$C_{20}$alkyl, —COO-aryl, CN, $CF_3$, F, $CH_2Cl$, $CH_2Br$; or the tetravalent linking group is a group of the formula

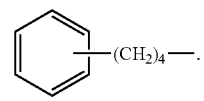

The term arylene used to define the divalent linking group refers to the following groups:

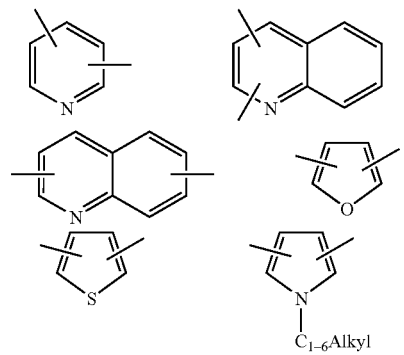

The above arylene groups may also contain more than 2 free bonds and are thus suitable as tri-or tetravalent linkers as well.

Concerning the linking groups, the term aryl as used in the groups O-aryl, —O—CO-aryl, —COO-aryl refers for example, to phenyl, naphthyl, biphenyl, anthracyl or phenanthryl.

When W has the meaning of —COO— or —CO—N($R_{15}$)—, the di-tri-or tetravalent linking group can also refer to structures like for example,

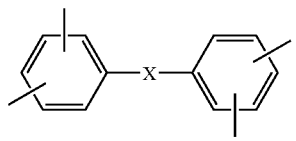

with  X=—$CH_2$—,  —$CF_2$—,  —CH($CH_3$)—, —C($CH_3$)$_3$—, —C($CF_3$)$_3$—, O, S, CO, SO, $SO_2$.

Preferably the linking group is a divalent linking group.

Depending on the group W, the following molecules are obtained:

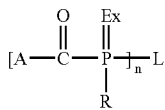 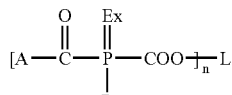

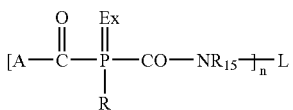

Preferred Compounds:
Of particular interest are compounds of the formula I

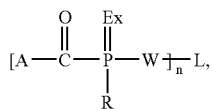

in which
E is O or S and x is 0 or 1;
A is a group

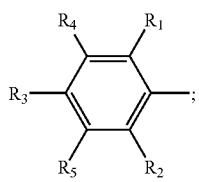

wherein
$R_1$ and $R_2$ independently of one another are $C_1$–$C_{12}$alkyl, $OR_{11}$, $CF_3$ or halogen;
$R_3$, $R_4$ and $R_5$ independently of one another are hydrogen, $C_1$–$C_{12}$alkyl, $OR_{11}$ or halogen;
R is $C_1$–$C_{12}$alkyl, unsubstituted or substituted by phenyl, CN, $OR_{11}$, $C(O)R_{11}$, $C(O)OR_{11}$, $C(O)N(R_{14})_2$;
$C_2$–$C_{12}$alkyl which is interrupted once or more than once by nonconsecutive O and which is unsubstituted or substituted by phenyl, CN, $OR_{11}$, $C(O)R_{11}$, $C(O)OR_{11}$, $C(O)N(R_{14})_2$;
$C_2$–$C_{12}$alkenyl which is uninterrupted or interrupted once or more than once by nonconsecutive O and which is unsubstituted or substituted by $OR_{11}$, $N(R_{12})(R_{13})$, or $C_1$–$C_{12}$alkyl;
benzyl;
$C_4$–$C_8$cycloalkyl which is uninterrupted or interrupted once or more than once by O, S or $NR_{14}$ and which is unsubstituted or substituted by $OR_{11}$, $SR_{11}$, $N(R_{12})(R_{13})$, or $C_1$–$C_{12}$alkyl;
$C_8$–$C_{12}$arylcycloalkyl; or;

R is a group of the formula

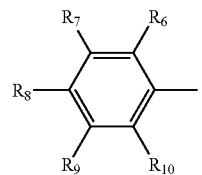

wherein
$R_6$, $R_7$, $R_8$, $R_9$ and $R_{10}$ independently of one another are hydrogen, $C_1$–$C_{12}$alkyl;
$OR_{11}$, phenyl or halogen;
W is a bond, —CO—O— or —CO—N($R_{15}$)—;
L is a di- or trivalent linking group,
n is a number of 2 or 3;
$R_{11}$ is hydrogen, $C_1$–$C_{12}$alkyl, $C_5$–$C_6$cycloalkyl, phenyl or benzyl;
$R_{12}$ and $R_{13}$ independently of one another are hydrogen, $C_1$–$C_{12}$alkyl, phenyl, benzyl or $C_2$–$C_{12}$alkyl which is interrupted once or more than once by nonconsecutive O atoms and which is unsubstituted or substituted by OH or SH; or $R_{12}$ and $R_{13}$ together are piperidino, morpholino or piperazino;;
$R_{14}$ is hydrogen, phenyl, $C_1$–$C_{12}$alkyl or $C_2$–$C_{12}$alkyl which is interrupted once or more than once by nonconsecutive O atoms and which is unsubstituted or substituted by OH or SH;
$R_{15}$ is hydrogen, $C_1$–$C_{12}$alkyl, phenyl unsubstituted or substituted once or more with $C_1$–$C_4$alkyl.

Especially preferred are compounds of the formula I

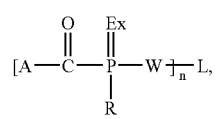

in which
E is O and x is 1;
A is a group

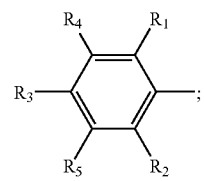

wherein
$R_1$ and $R_2$ independently of one another are $C_1$–$C_4$alkyl, $C_1$–$C_4$alkoxy, $CF_3$ or Cl;
$R_3$, $R_4$ and $R_5$ independently of one another are hydrogen, $C_1$–$C_4$alkyl, $C_1$–$C_4$alkoxy or Cl;
R is $C_1$–$C_{12}$alkyl, or;

R is a group of the formula

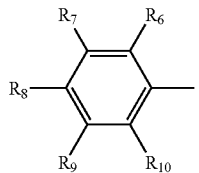

wherein
$R_6$, $R_7$, $R_8$, $R_9$ and $R_{10}$ independently of one another are hydrogen, $C_1$–$C_4$alkyl, $C_1$–$C_4$alkoxy, phenyl or Cl;
W is a bond;
L is a di-valent linking group,
n is a number of 2.

The compounds may be prepared starting from a compound of the formula II

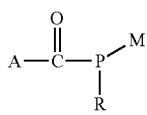

II wherein A and R are as described above and M is hydrogen, Li, Na, K, preferably Li.

Compounds of the formula II, wherein R=Ra and
Ra is $C_1$–$C_{24}$alkyl, unsubstituted or substituted by $C_3$–$C_{24}$cycloalkyl, $C_3$–$C_{24}$cycloalkenyl, phenyl, CN, $C(O)R_{11}$, $C(O)OR_{11}$, $C(O)N(R_{14})_2$, $OC(O)R_{11}$, $OC(O)OR_{11}$, $N(R_{14})C(O)N(R_{14})$, $OC(O)NR_{14}$, $N(R_{14})C(O)OR_{11}$, halogen, $OR_{11}$, $SR_{11}$ or $N(R_{12})(R_{13})$;

$C_2$–$C_{24}$alkyl which is interrupted once or more than once by nonconsecutive O, S or $NR_{14}$ and which is unsubstituted or substituted by phenyl, $OR_{11}$, $SR_{11}$, $N(R_{12})(R_{13})$, CN, $C(O)R_{11}$, $C(O)OR_{11}$, or $C(O)N(R_{14})_2$;

$C_2$–$C_{24}$alkenyl which is uninterrupted or interrupted once or more than once by nonconsecutive O, S or $NR_{14}$ and which is unsubstituted or substituted by $OR_{11}$, $SR_{11}$, $N(R_{12})(R_{13})$, or $C_1$–$C_{12}$alkyl;

$C_5$–$C_{24}$cycloalkenyl which is uninterrupted or interrupted once or more than once by nonconsecutive O, S or $NR_{14}$ and which is unsubstituted or substituted by $OR_{11}$, $SR_{11}$, $N(R_{12})(R_{13})$, or $C_1$–$C_{12}$alkyl;

$C_7$–$C_{24}$arylalkyl which is unsubstituted or substituted on the aryl group by $C_1$–$C_{12}$alkyl, $C_1$–$C_{12}$alkoxy or halogen;

$C_4$–$C_{24}$cycloalkyl which is uninterrupted or interrupted once or more than once by O, S or $NR_{14}$ and which is unsubstituted or substituted by $OR_{11}$, $SR_{11}$, $N(R_{12})(R_{13})$, or $C_1$–$C_{12}$alkyl;

$C_8$–$C_{24}$arylcycloalkyl or $C_8$–$C_{24}$arylcycloalkenyl;

are described in the British Patent Application 0112580.6 filed May, 24, 2001

Examples of compounds of the formula II as described in the British Patent Application 0112580.6 are: lithium (2,6-dimethylbenzoyl)ethylphosphine, lithium (2,6-diethylbenzoyl)ethylphosphine, lithium (2,4,6-trimethylbenzoyl)ethylphosphine, lithium (2,3,4,5,6-pentamethylbenzoyl)ethylphosphine, lithium (2,3,5,6-tetramethylbenzoyl)ethylphosphine, lithium (2,4,6-triisopropylbenzoyl)ethylphosphine, lithium (2,4,5,6-tetramethylbenzoyl)ethylphosphine, lithium (2,4,6-tri-tert-butylbenzoyl)ethylphosphine, lithium (2,6-dimethyl-4-tert-butylbenzoyl)ethylphosphine, lithium (2,6-diphenoxymethylbenzoyl)ethylphosphine, lithium (2,3,6-trimethylbenzoyl)ethylphosphine, lithium (2,3,4,6-tetramethylbenzoyl)ethylphosphine, lithium (2-phenyl-6-methylbenzoyl)ethylphosphine, lithium (2,4,6-trimethoxybenzoyl)ethylphosphine, lithium (2,4-dimethoxybenzoyl)ethylphosphine, lithium (2,3,6-trimethoxybenzoyl)ethylphosphine, lithium (2,6-diethoxybenzoyl)ethylphosphine, lithium (2,6-dimethoxy-3,5-dimethylbenzoyl)ethylphosphine, lithium (2,6-dimethoxy-4-methylbenzoyl)ethylphosphine, lithium (2,6-dimethoxy-3-bromobenzoyl)ethylphosphine, lithium (2,6-dimethoxy-3-chlorobenzoyl)ethylphosphine, lithium (2,6-dimethoxy-3-chloro-5-bromobenzoyl)ethylphosphine, lithium (2,6-dimethoxy-3,5-di-chlorobenzoyl)ethylphosphine, lithium (2,3,6-trimethoxy-5-bromobenzoyl)ethylphosphine, lithium (2,6-dichlorobenzoyl)ethylphosphine, lithium (2,4,6-trichlorobenzoyl)ethylphosphine, lithium (2,3,6-trichlorobenzoyl)ethylphosphine, lithium (2,3,5,6-tetrachlorobenzoyl)ethylphosphine, lithium (2,3,4,5,6-pentachlorobenzoyl)ethylphosphine, lithium (2,6-dichloro-3-methylbenzoyl)ethylphosphine, lithium (2-chloro-6-methylbenzoyl)ethylphosphine, lithium (2-methoxy-3,6-dichlorobenzoyl)ethylphosphine, lithium (2-methoxy-6-chlorobenzoyl)ethylphosphine, lithium (2,6-bis(trifluoromethyl)benzoyl)ethylphosphine, lithium (2-chloro-6-methylthiobenzoyl)ethylphosphine, lithium (2,6-dibromobenzoyl)ethylphosphine, lithium (2,6-dimethylbenzoyl)-n-butylphosphine, lithium (2,6-diethylbenzoyl)-n-butylphosphine, lithium (2,4,6-trimethylbenzoyl)-n-butylphosphine, lithium (2,3,4,5,6-pentamethylbenzoyl)-n-butylphosphine, lithium (2,3,5,6-tetramethylbenzoyl)-n-butylphosphine, lithium (2,4,6-triisopropylbenzoyl)-n-butylphosphine, lithium (2,4,5,6-tetramethylbenzoyl)-n-butylphosphine, lithium (2,4,6-tri-tert-butylbenzoyl)-n-butylphosphine, lithium (2,6-dimethyl-4-tert-butylbenzoyl)-n-butylphosphine, lithium (2,6-diphenoxymethylbenzoyl)-n-butylphosphine, lithium (2,3,6-trimethylbenzoyl)-n-butylphosphine, lithium (2,3,4,6-tetramethylbenzoyl)-n-butylphosphine, lithium (2-phenyl-6-methylbenzoyl)-n-butylphosphine, lithium (2,4,6-trimethoxybenzoyl)-n-butylphosphine, lithium (2,4-dimethoxybenzoyl)-n-butylphosphine, lithium (2,3,6-trimethoxybenzoyl)-n-butylphosphine, lithium (2,6-diethoxybenzoyl)-n-butylphosphine, lithium (2,6-dimethoxy-3,5-dimethylbenzoyl)-n-butylphosphine, lithium (2,6-dimethoxy-4-methylbenzoyl)-n-butylphosphine, lithium (2,6-dimethoxy-3-bromobenzoyl)-n-butylphosphine, lithium (2,6-dimethoxy-3-chlorobenzoyl)-n-butylphosphine, lithium (2,6-dimethoxy-3-chloro-5-bromobenzoyl)-n-butylphosphine, lithium (2,6-dimethoxy-3,5-dichlorobenzoyl)-n-butylphosphine, lithium (2,3,6-trimethoxy-5-bromobenzoyl)-n-butylphosphine, lithium (2,6-dichlorobenzoyl)-n-butylphosphine, lithium (2,4,6-trichlorobenzoyl)-n-butylphosphine, lithium (2,3,6-trichlorobenzoyl)-n-butylphosphine, lithium (2,3,5,6-tetrachlorobenzoyl)-n-butylphosphine, lithium (2,3,4,5,6-pentachlorobenzoyl)-n-butylphosphine, lithium (2,6-dichloro-3-methylbenzoyl)-n-butylphosphine, lithium (2-chloro-6-methylbenzoyl)-n-butylphosphine, lithium (2-methoxy-3,6-dichlorobenzoyl)-n-butylphosphine, lithium (2-methoxy-6-chlorobenzoyl)-n-butylphosphine, lithium (2,6-bis(trifluoromethyl)benzoyl)-n-butylphosphine, lithium (2-chloro-6-methylthiobenzoyl)-n-butylphosphine, lithium (2,6-dibromobenzoyl)-n-butylphosphine, lithium (2,6-dimethylbenzoyl)isobutylphosphine, lithium (2,6-diethylbenzoyl)isobutylphosphine, lithium (2,4,6-trimethylbenzoyl)isobutylphosphine, lithium (2,3,4,5,6-pentamethylbenzoyl)isobutylphosphine, lithium (2,3,5,6-tetramethylbenzoyl)isobutylphosphine, lithium (2,4,6-triisopropylbenzoyl)isobutylphosphine, lithium (2,4,5,6-tetramethylbenzoyl)isobutylphosphine, lithium (2,4,6-tri-tert-butylbenzoyl)isobutylphosphine, lithium (2,6-dimethyl-4-tert-butylbenzoyl)isobutylphosphine, lithium (2,6-diphenoxymethylbenzoyl)isobutylphosphine, lithium (2,3,6-trimethylbenzoyl)isobutylphosphine, lithium (2,3,4,6-tetramethylbenzoyl)isobutylphosphine, lithium (2-phenyl-6-methylbenzoyl)isobutylphosphine, lithium (2,4,6-trimethoxybenzoyl)isobutylphosphine, lithium (2,4-dimethoxybenzoyl)isobutylphosphine, lithium (2,3,6-trimethoxybenzoyl)isobutylphosphine, lithium (2,6-diethoxybenzoyl)isobutylphosphine, lithium (2,6-dimethoxy-3,5-dimethylbenzoyl)isobutylphosphine, lithium (2,6-dimethoxy-4-methylbenzoyl)isobutylphosphine, lithium (2,6-dimethoxy-3-bromobenzoyl)isobutylphosphine, lithium (2,6-dimethoxy-3-chlorobenzoyl)isobutylphosphine, lithium (2,6-dimethoxy-3-chloro-5-bromobenzoyl)isobutylphosphine, lithium (2,6-dimethoxy-3,5-dichlorobenzoyl)isobutylphosphine, lithium (2,3,6-trimethoxy-5-bromobenzoyl)isobutylphosphine, lithium (2,6-dichlorobenzoyl)isobutylphosphine, lithium (2,4,6-trichlorobenzoyl)isobutylphosphine, lithium (2,3,6-trichlorobenzoyl)isobutylphosphine, lithium (2,3,5,6-tetrachlorobenzoyl)isobutylphosphine, lithium (2,3,4,5,6-pentachlorobenzoyl)isobutylphosphine, lithium (2,6-dichloro-3-methylbenzoyl)isobutylphosphine, lithium (2-chloro-6-methylbenzoyl)isobutylphosphine, lithium (2-methoxy-3,6-dichlorobenzoyl)isobutylphosphine, lithium (2-methoxy-6-chlorobenzoyl)isobutylphosphine, lithium (2,6-bis(trifluoromethyl)-benzoyl)isobutylphosphine, lithium (2-chloro-6-methylthiobenzoyl)isobutylphosphine, lithium (2,6-dibromobenzoyl)isobutylphosphine, lithium (2,6-dimethylbenzoyl)-1-methylpropylphosphine, lithium (2,6-diethylbenzoyl)-1-methylpropylphosphine, lithium (2,4,6-trimethylbenzoyl)-1-methylpropylphosphine, lithium (2,3,4,5,6-pentamethylbenzoyl)-1-methylpropylphosphine, lithium (2,3,5,6-tetramethylbenzoyl)-1-methylpropylphosphine, lithium (2,4,6-triisopropylbenzoyl)-1-methylpropylphosphine, lithium (2,4,5,6-tetramethylbenzoyl)-1-methylpropylphosphine, lithium (2,4,6-tri-tert-butylbenzoyl)-1-methylpropylphosphine, lithium (2,6-dimethyl-4tert-butylbenzoyl)-1-methylpropylphosphine, lithium (2,6-diphenoxymethylbenzoyl)-1-methylpropylphosphine, lithium (2,3,6-trimethylbenzoyl)-1-methylpropylphosphine, lithium (2,3,4,6-tetramethylbenzoyl)-1-methylpropylphosphine, lithium (2-phenyl-6-methylbenzoyl)-1-methylpropylphosphine, lithium (2,4,6-trimethoxybenzoyl)-1-methylpropylphosphine, lithium (2,4-dimethoxybenzoyl)-1-methylpropylphosphine, lithium (2,3,6-trimethoxybenzoyl)-1-methylpropylphosphine, lithium (2,6-diethoxybenzoyl)-1-methylpropylphosphine, lithium (2,6-dimethoxy-3,5-dimethylbenzoyl)-1-methylpropylphosphine, lithium (2,6-dimethoxy-4-methylbenzoyl)-1-methylpropylphosphine, lithium (2,6-dimethoxy-3-bromobenzoyl)-1-methylpropylphosphine, lithium (2,6-dimethoxy-3-chlorobenzoyl)-1-methylpropylphosphine, lithium (2,6-dimethoxy-3-chloro-5-bromobenzoyl)-1-methylpropylphosphine, lithium (2,6-dimethoxy-3,5-dichlorobenzoyl)-1-methylpropylphosphine, lithium (2,3,6-trimethoxy-5-bromobenzoyl)-1-methylpropylphosphine, lithium (2,6-dichlorobenzoyl)-1-methylpropylphosphine, lithium (2,4,6-trichlorobenzoyl)-1-methylpropylphosphine, lithium (2,3,6-trichlorobenzoyl)-1-methylpropylphosphine, lithium (2,3,5,6-tetrachlorobenzoyl)-1-methylpropylphosphine, lithium (2,3,4,5,6-pentachlorobenzoyl)-1-methylpropylphosphine, lithium (2,6-dichloro-3-methylbenzoyl)-1-methylpropylphosphine, lithium (2-chloro-6-methylbenzoyl)-1-methylpropylphosphine, lithium (2-methoxy-3,6-dichlorobenzoyl)-1-methylpropylphosphine, lithium (2-methoxy-6-chlorobenzoyl)-1-methylpropylphosphine, lithium (2,6-bis-(trifluoromethyl)benzoyl)-1-methylpropylphosphine, lithium (2-chloro-6-methylthiobenzoyl)-1-methylpropylphosphine, lithium (2,6-dibromobenzoyl)-1-methylpropylphosphine, lithium (2,6-dimethylbenzoyl)-2,4,4-trimethylpentylphosphine, lithium (2,6-diethylbenzoyl)-2,4,4-trimethylpentylphosphine, lithium (2,4,6-trimethylbenzoyl)-2,4,4-trimethylpentylphosphine, lithium (2,3,4,5,6-pentamethylbenzoyl)-2,4,4-trimethylpentylphosphine, lithium (2,3,5,6-tetramethylbenzoyl)-2,4,4-trimethylpentylphosphine, lithium (2,4,6-triisopropylbenzoyl)-2,4,4-tri-methylpentylphosphine, lithium (2,4,5,6-tetramethylbenzoyl)-2,4,4-trimethylpentylphosphine, lithium (2,4,6-tri-tert-butylbenzoyl)-2,4,4-trimethylpentylphosphine, lithium (2,6-dimethyl-4-tert-butylbenzoyl)-2,4,4-trimethylpentylphosphine, lithium (2,6-diphenoxymethylbenzoyl)-2,4,4-trimethylpentylphosphine, lithium (2,3,6-trimethylbenzoyl)-2,4,4-trimethylpentylphosphine, lithium (2,3,4,6-tetramethylbenzoyl)-2,4,4-trimethylpentylphosphine, lithium (2-phenyl-6-methylbenzoyl)-2,4,4-trimethylpentylphosphine, lithium (2,4,6-trimethoxybenzoyl)-2,4,4-trimethylpentylphosphine, lithium (2,4-dimethoxybenzoyl)-2,4,4-trimethylpentylphosphine, lithium (2,3,6-trimethoxybenzoyl)-2,4,4-trimethylpentylphosphine, lithium (2,6-diethoxybenzoyl)-2,4,4-trimethylpentylphosphine, lithium (2,6-dimethoxy-3,5-dimethylbenzoyl)-2,4,4-trimethylpentylphosphine, lithium (2,6-dimethoxy-4-methylbenzoyl)-2,4,4-trimethylpentylphosphine, lithium (2,6-dimethoxy-3-bromobenzoyl)-2,4,4-trimethylpentylphosphine, lithium (2,6-dimethoxy-3-chlorobenzoyl)-2,4,4-trimethylpentylphosphine, lithium (2,6-dimethoxy-3-chloro-5-bromobenzoyl)-2,4,4-trimethylpentylphosphine, lithium (2,6-dimethoxy-3,5-dichlorobenzoyl)-2,4,4-trimethylpentylphosphine, lithium (2,3,6-trimethoxy-5-bromobenzoyl)-2,4,4-trimethylpentylphosphine, lithium (2,6-dichlorobenzoyl)-2,4,4-trimethylpentylphosphine, lithium (2,4,6-trichlorobenzoyl)-2,4,4-trimethylpentylphosphine, lithium (2,3,6-trichlorobenzoyl)-2,4,4-trimethylpentylphosphine, lithium (2,3,5,6-tetrachlorobenzoyl)-2,4,4-trimethylpentylphosphine, lithium (2,3,4,5,6-pentachlorobenzoyl)-2,4,4-trimethylpentylphosphine, lithium (2,6-dichloro-3-methylbenzoyl)-2,4,4-trimethylpentylphosphine, lithium (2-chloro-6-methylbenzoyl)-2,4,4-trimethylpentylphosphine, lithium (2-methoxy-3,6-dichlorobenzoyl)-2,4,4-trimethylpentylphosphine, lithium (2-methoxy-6-chlorobenzoyl)-2,4,4-trimethylpentylphosphine, lithium (2,6-bis(trifluoromethyl)benzoyl)-2,4,4-trimethylpentylphosphine, lithium (2-chloro-6-methylthiobenzoyl)-2,4,4-trimethylpentylphosphine, lithium (2,6-dibromobenzoyl)-2,4,4-trimethylpentylphosphine, lithium (2,6-dimethylbenzoyl)cyclopentylphosphine, lithium (2,6-diethylbenzoyl)cyclopentylphosphine, lithium (2,4,6-trimethylbenzoyl)cyclopentylphosphine, lithium (2,3,4,5,6-pentamethylbenzoyl)cyclopentylphosphine, lithium (2,3,5,6-tetramethylbenzoyl)cyclopentylphosphine, lithium (2,4,6-triisopropylbenzoyl)cyclopentylphosphine, lithium (2,4,5,6-tetramethylbenzoyl)cyclopentylphosphine, lithium (2,4,6-tri-tert-butylbenzoyl)cyclopentylphosphine, lithium (2,6-dimethyl-4-tert-butylbenzoyl)cyclopentylphosphine, lithium (2,6-diphenoxymethylbenzoyl)cyclopentylphosphine, lithium (2,3,6-trimethylbenzoyl)cyclopentylphosphine, lithium (2,3,4,6-tetramethylbenzoyl)cyclopentylphosphine, lithium (2-phenyl-6-methylbenzoyl)cyclopentylphosphine, lithium (2,4,6-trimethoxybenzoyl)cyclopentylphosphine, lithium (2,4-dimethoxybenzoyl)cyclopentylphosphine, lithium (2,3,6-trimethoxybenzoyl)cyclopentylphosphine, lithium (2,6-diethoxybenzoyl)cyclopentylphosphine, lithium (2,6-dimethoxy-3,5-dimethylbenzoyl)cyclopentylphosphine, lithium (2,6-dimethoxy-4-methylbenzoyl)cyclopentylphosphine, lithium (2,6-dimethoxy-3-bromobenzoyl)cyclopentylphosphine, lithium (2,6-dimethoxy-3-chlorobenzoyl)cyclopentylphosphine, lithium (2,6-dimethoxy-3-chloro-5-bromobenzoyl)cyclopentylphosphine, lithium (2,6-dimethoxy-3,5-dichlorobenzoyl)cyclopentylphosphine, lithium (2,3,6-trimethoxy-5-bromobenzoyl)cyclopentylphosphine, lithium (2,6-dichlorobenzoyl)cyclopentylphosphine, lithium (2,4,6-trichlorobenzoyl)cyclopentylphosphine, lithium (2,3,6-trichlorobenzoyl)cyclopentylphosphine, lithium (2,3,5,6-tetrachlorobenzoyl)cyclopentylphosphine, lithium (2,3,4,5,6-pentachlorobenzoyl)cyclopentylphosphine, lithium (2,6-dichloro-3-methylbenzoyl)cyclopentylphosphine, lithium (2-chloro-6-methylbenzoyl)cyclopentylphosphine, lithium (2-methoxy-3,6-dichlorobenzoyl)cyclopentylphosphine, lithium (2-methoxy-6-chlorobenzoyl)-cyclopentylphosphine, lithium (2,6-bis(trifluoromethyl)benzoyl)cyclopentylphosphine, lithium (2-chloro-6-methylthiobenzoyl)cyclopentylphosphine, lithium (2,6-dibromobenzoyl)cyclopentylphosphine, lithium (2,6-dimethylbenzoyl)cyclohexylphosphine, lithium (2,6-diethylbenzoyl)cyclohexylphosphine, lithium (2,4,6-trimethylbenzoyl)cyclohexylphosphine, lithium (2,3,4,5,6-pentamethylbenzoyl)cyclohexylphosphine, lithium (2,3,5,6-tetramethylbenzoyl)cyclohexylphosphine, lithium (2,4,6-triisopropylbenzoyl)cyclohexylphosphine, lithium (2,4,5,6-tetramethylbenzoyl)cyclohexylphosphine, lithium (2,4,6-tri-tert-butylbenzoyl)cyclohexylphosphine, lithium (2,6-dimethyl-4-tert-butylbenzoyl)cyclohexylphosphine, lithium (2,6-diphenoxymethylbenzoyl)cyclohexylphosphine, lithium (2,3,6-trimethylbenzoyl)cyclohexylphosphine, lithium (2,3,4,6-tetramethylbenzoyl)cyclohexylphosphine, lithium (2-phenyl-6-methylbenzoyl)cyclohexylphosphine, lithium (2,4,6-trimethoxybenzoyl)cyclohexylphosphine, lithium (2,4-dimethoxybenzoyl)cyclohexylphosphine, lithium (2,3,6-trimethoxybenzoyl)cyclohexylphosphine, lithium (2,6-diethoxybenzoyl)cyclohexylphosphine, lithium (2,6-dimethoxy-3,5-dimethylbenzoyl)cyclohexylphosphine, lithium (2,6-dimethoxy-4-methylbenzoyl)cyclohexylphosphine, lithium (2,6-dimethoxy-3-bromobenzoyl)cyclohexylphosphine, lithium (2,6-dimethoxy-3-chlorobenzoyl)cyclohexylphosphine, lithium (2,6-dimethoxy-3-chloro-5-bromobenzoyl)cyclohexylphosphine, lithium (2,6-dimethoxy-3,5-dichlorobenzoyl)cyclohexylphosphine, lithium (2,3,6-trimethoxy-5-bromobenzoyl)cyclohexylphosphine, lithium (2,6-dichlorobenzoyl)cyclohexylphosphine, lithium (2,4,6-trichlorobenzoyl)cyclohexylphosphine, lithium (2,3,6-trichlorobenzoyl)cyclohexylphosphine, lithium (2,3,5,6-tetrachlorobenzoyl)cyclohexylphosphine, lithium (2,3,4,5,6-pentachlorobenzoyl)cyclohexylphosphine, lithium (2,6-dichloro-3-methylbenzoyl)cyclohexylphosphine, lithium (2-chloro-6-methylbenzoyl)cyclohexylphosphine, lithium (2-methoxy-3,6-dichlorobenzoyl)cyclohexylphosphine, lithium (2-methoxy-6-chlorobenzoyl)cyclohexylphosphine, lithium (2,6-bis(trifluoromethyl)benzoyl)cyclohexylphosphine, lithium (2-chloro-6-methylthiobenzoyl)cyclohexylphosphine, lithium (2,6-dibromobenzoyl)cyclohexylphosphine.

The preparation of the compounds of formula II as described in the British Patent Application 0112580.6 can be summarized as follows:

(1) Reaction of an acyl halide of the formula IV

(IV)

in which

A is as defined above and X is Cl or Br;

with a dimetalated organophosphine of the formula V

(V)

in which $R_a$ is as defined above and $M_1$ is Na, Li or K in the molar ratio 1:1; and (2) where appropriate, subsequent hydrolysis if compounds of the formula II in which M is hydrogen are to be obtained.

The starting materials are advantageously reacted in the molar ratio 1:1. A slight excess of one or the other of the components, e.g. up to 20%, is not critical. In this case the desired product is formed too, although the proportion of undesired byproducts may be influenced.

The reaction is advantageously carried out in a solvent. In particular, as solvents, it is possible to use ethers which are liquid at atmospheric pressure and room temperature. Examples are dimethyl ether, diethyl ether, methyl propyl ether, 1,2-dimethoxyethane, bis(2-methoxyethyl)ether, dioxane or tetrahydrofuran. Preference is given to using tetrahydrofuran.

The reaction temperatures are advantageously −60° C. to +120° C., e.g. −40° C. to 100° C., for example −20° C. to +80° C.

It is advisable to stir the reaction mixture.

It is advantageous to initially introduce the compound of the formula V and to add dropwise the compound of the formula IV at the temperatures given above. Here, the compound of the formula IV can be added without a diluent or else diluted with the reaction solvent. If desired, the course of the reaction can be monitored using methods customary in the art, for example NMR, for example $^{31}$P-NMR, chromatography (thin-layer, HPLC, GC) etc. In the reactions described above, it is essential to work in an inert gas atmosphere, e.g. with a protective gas such as argon or nitrogen, in order to exclude atmospheric oxygen.

The acyl halides (IV) used as starting material are known substances, some of which are available commercially, or can be prepared analogously to known compounds.

A method for the preparation of metalated alkylphosphines is, for example, the reaction of suitable alkylphosphines with the corresponding alkali metal, alkali metal hydride or an alkyl-lithium compound.

Compounds of the formula II, wherein R=Rb and Rb is a group of the formula

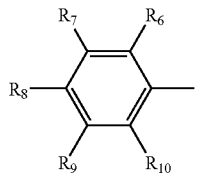

wherein

R_6, R_7, R_8, R_9 and R_10 independently of one another are hydrogen, $C_1$–$C_{24}$alkyl;

$C_2$–$C_{24}$alkyl which is interrupted once or more than once by nonconsecutive O, S or NR_14 and which is unsubstituted or substituted by OH, SH; SR_11, or N(R_12)(R_13), OR_11, phenyl or halogen;

are described in the German Patent Publication DE OS 10105046, published Aug. 9, 2001.

The preparation of the compounds of formula II as described in the German Patent Publication DE OS 10105046 can be summarized as follows:

(1) Reaction of an acyl halide of the formula IV

in which

A is as defined above and X is Cl or Br;

with a dimetalated arylphosphine of the formula V'

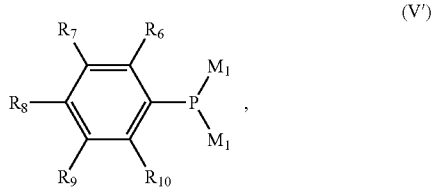

in which

R_6, R_7, R_8, R_9 and R_10 are as defined above and Ml is Na, Li or K in the molar ratio 1:1; and (2) where appropriate, subsequent hydrolysis if compounds of the formula I in which M is hydrogen are to be obtained.

The starting materials are advantageously reacted in the molar ratio 1:1. A slight excess of one or an other of the components, e.g. up to 20%, is not critical. In this case the desired product is formed too, although the proportion of undesired byproducts may be influenced.

The reaction is advantageously carried out in a solvent. In particular, as solvents, it is possible to use ethers which are liquid at atmospheric pressure and room temperature. Examples are dimethyl ether, diethyl ether, methyl propyl ether, 1,2-dimethoxyethane, bis(2-methoxyethyl)ether, dioxane or tetrahydrofuran. Preference is given to using tetrahydrofuran.

The reaction temperatures are advantageously −60° C. to +120° C., e.g. −40° C. to 100° C., for example −20° C. to +80° C.

It is advisable to stir the reaction mixture.

It is advantageous to initially introduce the compound of the formula V and to add dropwise the compound of the formula IV at the temperatures given above.

Here, the compound of the formula IV can be added without a diluent or else diluted with the reaction solvent.

If desired, the course of the reaction can be monitored using methods customary in the art, for example NMR, for example $^{31}$P-NMR, chromatography (thin-layer, HPLC, GC) etc.

In the reactions described above, it is essential to work in an inert gas atmosphere, e.g. with a protective gas such as argon or nitrogen, in order to exclude atmospheric oxygen.

The acyl halides (IV) used as starting material are known substances, some of which are available commercially, or can be prepared by analogy with known compounds.

The preparation of the metalated arylphosphines (V'), can, for example, be carried out by reacting suitable phosphorus halides (preparation of which is known and disclosed, for example, by W. Davies in J. Chem. Soc. (1935), 462 and J. Chem. Soc. (1944), 276 with the corresponding alkali metal.

In order to prepare the compounds of formula I with x=0, the compounds of formula II

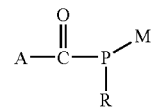

are reacted analog as performed in the German Patent Publication DE OS 10105046 with a linking compound Hal-L-[Hal]_m or Hal-W-L-[W-Hal]_m wherein L, W and Hal are as defined above and m is 1, 2 or 3. Depending if a di-,tri-or tetravalent linking group is used, the ratio of the educts varies from 2:1 to 4:1. A slight excess of one or the other educt, e.g. up to 20%, is no critical. In this case the desired product is formed too, although the proportion of undesired byproducts may be influenced.

The compounds of formula I with x=1 and E=O are prepared by oxidation of the corresponding phosphines (compounds of formula I with x=0).

The oxidation of the phosphine is carried out using oxidizing agents customary in the art. Suitable oxidizing agents are primarily hydrogen peroxide and organic peroxy compounds, for example peracetic acid or t-butyl hydroperoxide, air or pure oxygen.

The oxidation is advantageously carried out in solution. Suitable solvents are aromatic hydrocarbons, for example benzene, toluene, m-xylene, p-xylene, ethylbenzene or mesitylene, or aliphatic hydrocarbons, e.g. alkanes and alkane mixtures, such as petroleum ether, hexane or cyclohexane. Further suitable examples are dimethyl ether, diethyl ether, methyl propyl ether, 1,2-dimethoxyethane, bis(2-methoxyethyl)ether, dioxane or tetrahydrofuran. Preference is given to using toluene.

The reaction temperature during the oxidation is advantageously kept between 0° and 120° C., preferably between 200 and 80° C.

The reaction products of the formula (I) with x=1 and E=O can be isolated and purified by customary processing measures familiar to the person skilled in the art.

The compounds of formula I with x=1 and E=S are prepared by sulfuration of the corresponding phosphines (compounds of formula I with x=0).

The preparation of the respective sulfide is carried out by reaction with sulfur. The compounds of formula I with x=1 and E=O are here reacted with an equimolar to 2-fold molar amount of elemental sulfur e.g. without a diluent or optionally in a suitable inert organic solvent. Examples of suitable solvents are those described for the oxidation reaction. It is, however, also possible to use, for example, aliphatic or aromatic ethers, for example dibutyl ether, dioxane, diethylene glycol dimethyl ether or diphenyl ether at temperatures from 20° to 250° C., preferably 60° to 120° C. The resulting acylphosphine sulfide, or its solution is advantageously freed from any elemental sulfur which may still be present by filtration. Following removal of the solvent, the acylphosphine sulfide can be isolated in pure form by distillation, recrystallization or chromatographic separation methods.

It is advantageous to carry out all of the reactions described above with the exclusion of air in an inert gas atmosphere, e.g. under nitrogen or argon gas. Moreover, stirring of the respective reaction mixture is advantageously appropriate.

The phosphines can either be isolated via known isolation and purification techniques prior to the oxidation or sulfuration step or can directly be oxidized or sulfurized without isolation.

According to the invention, the compounds of the formula I can be used as photoinitiators for the photopolymerization of ethylenically unsaturated compounds or mixtures which comprise such compounds. The compounds of the formula I can be used in combination with other photoinitiators or other additives.

The invention thus also relates to photopolymerizable compositions comprising
(a) at least one ethylenically unsaturated photopolymerizable compound and
(b) as photoinitiator, at least one compound of the formula I, where the composition, in addition to the component (b), can also comprise other photo-initiators (c) or other additives (d).

The unsaturated compounds can contain one or more olefinic double bonds. They can be of low molecular weight (monomeric) or relatively high molecular weight (oligomeric). Examples of monomers with a double bond are alkyl or hydroxyalkyl acrylates or methacrylates, for example methyl acrylate, ethyl acrylate, butyl acrylate, 2-ethylhexyl acrylate or 2-hydroxyethyl acrylate, isobornyl acrylate, methyl methacrylate or ethyl methacrylate. Also of interest are silicon- or fluorine-modified resins, e.g. silicone acrylates. Further examples are acrylonitrile, acrylamide, methacrylamide, N-substituted (meth)acrylamides, vinyl esters, such as vinyl acetate, vinyl ethers, such as isobutyl vinyl ether, styrene, alkyl- and halostyrenes, N-vinylpyrrolidone, vinyl chloride or vinylidene chloride.

Examples of monomers having two or more double bonds are ethylene glycol diacrylate, propylene glycol diacrylate, neopentyl glycol diacrylate, hexamethylene glycol diacrylate or bisphenol A diacrylate, 4,4'-bis(2-acryloyloxyethoxy) diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl)isocyanurate.

Examples of higher molecular weight (oligomeric) poly-unsaturated compounds are acrylicized epoxy resins, polyurethanes, polyethers and polyesters which are acrylicized or contain vinyl ether or epoxy groups. Further examples of unsaturated oligomers are unsaturated polyester resins which are mostly prepared from maleic acid, phthalic acid and one or more diols and have molecular weights of from about 500 to 3,000. In addition, it is also possible to use vinyl ether monomers and oligomers, and maleate-terminated oligomers having polyester, polyurethane, polyether, polyvinyl ether and epoxy main chains. In particular, combinations of oligomers which carry vinyl ether groups and polymers as described in WO 90/01512 are highly suitable. However, copolymers of vinyl ether and maleic acid-functionalized monomers are also suitable. Such unsaturated oligomers may also be referred to as prepolymers.

Examples of particularly suitable compounds are esters of ethylenically unsaturated carboxylic acids and polyols or polyepoxides, and polymers containing ethylenically unsaturated groups in the chain or in side-groups, for example unsaturated polyesters, polyamides and polyurethanes and copolymers thereof, alkyd resins, polybutadiene and butadiene copolymers, polyisoprene and isoprene copolymers, polymers and copolymers containing (meth)acrylic groups in side chains, and mixtures of one or more such polymers.

Examples of unsaturated carboxylic acids are acrylic acid, methacrylic acid, crotonic acid, itaconic acid, cinnamic acid, unsaturated fatty acids such as linolenic acid or oleic acid. Preference is given to acrylic acid and methacrylic acid.

Suitable polyols are aromatic and, in particular, aliphatic and cycloaliphatic polyols. Examples of aromatic polyols are hydroquinone, 4,4'-dihydroxydiphenyl, 2,2-di(4-hydroxyphenyl)propane, and also novolaks and resols. Examples of polyepoxides are those based on said polyols, particularly aromatic polyols and epichlorohydrins. In addition, polymers and copolymers which contain hydroxyl groups in the polymer chain or in side groups, for example polyvinyl alcohol and copolymers thereof or hydroxyalkyl polymethacrylates or copolymers thereof, are also suitable as polyols. Further suitable polyols are oligoesters containing hydroxyl end-groups.

Examples of aliphatic and cycloaliphatic polyols are alkylenediols having, preferably, 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of, preferably, 200 to 1,500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or completely esterified using one or different unsaturated carboxylic acids, where the free hydroxyl groups in partial esters may be modified, e.g. etherified or esterified with other carboxylic acids.

Examples of esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, dipropylenglycoldiacrylat, tripropylenglycoldiacrylat, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and triacrylate, 1,4-cyclohexane diacrylate, bisacrylates and bismethacrylates of polyethylene glycol having molecular weights of from 200 to 1,500, or mixtures thereof.

Furthermore the following esters are suitable: 1,6-hexanediol diacrylate, glycerine ethoxylate triacrylate, glycerine propoxylate triacrylate, trimethylolpropane ethoxylate triacrylate, trimethylolpropane propoxylate triacrylate, pentaerythritethoxylate tetraacrylate, pentaerythritpropoxylate triacrylate, pentaerythritpropoxylate tetraacrylate, neopentylglycolethoxylate diacrylate, neopentylglycolpropoxylate diacrylate.

Also suitable as component (a) are the amides of identical or different unsaturated carboxylic acids of aromatic, cycloaliphatic and aliphatic polyamines having, preferably, 2 to 6, particularly 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)ethane or di(β-aminopropoxy)ethane. Further suitable polyamines are polymers and copolymers with or without additional amino groups in the side chain and oligoamides containing amino end groups. Examples of such unsaturated amides are: methylenebisacrylamide, 1,6-hexamethylenebisacrylamide, diethylenetriaminetrismethacrylamide, bis(methacrylamidopropoxy)ethane, β-methacrylamidoethyl methacrylate, N[(β-hydroxyethoxy)ethyl]acrylamide.

Suitable unsaturated polyesters and polyamides are derived, for example, from maleic acid and diols or diamines. Some of the maleic acid may be replaced by other dicarboxylic acids. They can be used together with ethylenically unsaturated comonomers, e.g. styrene. The polyesters and polyamides may also be derived from dicarboxylic acids and ethylenically unsaturated diols or diamines, particularly from relatively long chain compounds containing, for example, 6 to 20 carbon atoms. Examples of polyurethanes are those constructed from saturated or unsaturated diisocyanates and unsaturated or saturated diols.

Polybutadiene and polyisoprene and copolymers thereof are known. Suitable comonomers are, for example, olefins, such as ethylene, propene, butene, hexene, (meth)acrylates, acrylonitrile, styrene or vinyl chloride. Polymers containing (meth)acrylate groups in the side chain are likewise known. These may, for example, be products of the reaction of novolak-based epoxy resins with (meth)acrylic acid, homo- or copolymers of vinyl alcohol or hydroxyalkyl derivatives thereof which have been esterified using (meth)acrylic acid, or homo- and copolymers of (meth)acrylates which have been esterified using hydroxyalkyl(meth)acrylates.

The photopolymerizable compounds may be used on their own or in any desired mixtures. Preference is given to using mixtures of polyol (meth)acrylates.

It is also possible to add binders to the compositions according to the invention; this is particularly advantageous if the photopolymerizable compounds are liquid or viscose substances. The amount of binder may, for example, be 5–95% by weight, preferably 10–90% by weight and particularly 40–90% by weight, based on the total solids. The binder is chosen depending on the field of application and on the properties required therefore, such as the facility for development in aqueous or organic solvent systems, adhesion to substrates and sensitivity to oxygen.

Examples of suitable binders are polymers having a molecular weight of from about 5,000–2,000,000, preferably 10,000–1,000,000. Examples are: homo- and copolymeric acrylates and methacrylates, e.g. copolymers of methyl methacrylate/ethyl acrylate/methacrylic acid, poly(alkyl methacrylates), poly(alkyl acrylates); cellulose esters and cellulose ethers, such as cellulose acetate, cellulose acetate butyrate, methylcellulose, ethylcellulose; polyvinylbutyral, polyvinylformal, cyclized rubber, polyethers, such as polyethylene oxide, polypropylene oxide, polytetrahydroturan; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethyleneadipamide), and polyesters such as poly(ethylene glycol terephthalate) and poly(hexamethylene glycol succinate).

The unsaturated compounds can also be used in mixtures with non-photopolymerizable film-forming components. These may, for example, be physically drying polymers or solutions thereof in organic solvents, for example nitrocellulose or cellulose acetobutyrate. However, they may also be chemically or thermally curable resins, for example polyisocyanates, polyepoxides or melamine resins. The co-use of thermally curable resins is of importance for use in so-called hybrid systems, which are photopolymerized in a first stage and are crosslinked by thermal aftertreatment in a second stage.

The photoinitiators according to the invention are also suitable as initiators for the curing of oxidatively drying systems, as are described, for example, in Lehrbuch der Lacke und Beschichtungen Volume III, 296–328, Verlag W. A. Colomb in Heenemann GmbH, Berlin-Oberschwandorf (1976).

Apart from the photoinitiator, the photopolymerizable mixtures can also contain various additives (d). Examples thereof are thermal inhibitors, which are intended to prevent premature polymerization, for example hydroquinone, hydroquinone derivatives, p-methoxyphenol, β-naphthol or sterically hindered phenols, for example 2,6-di(tert-butyl)-p-cresol. To increase the storage stability in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. In order to exclude atmospheric oxygen during the polymerization, it is possible to add paraffin or similar wax-like substances which migrate to the surface at the start of the polymerization due to their lack of solubility in the polymers, and form a transparent surface layer which prevents the entry of air. It is likewise possible to apply an oxygen-impermeable layer. Light protection agents which may be used are UV absorbers, for example those of the hydroxyphenylbenzotriazol, hydroxyphenylbenzophenone, oxalamide or hydroxyphenyl-s-triazine type. The compounds can be used individually or as mixtures, with or without the use of sterically hindered amines (HALS).

Examples of such UV absorbers and light protection agents are 1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy4'-octoxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole. 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethyl-hexyloxy) carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonyl-ethyl)phenylbenzotriazole, 2,2'-methylenebis[4-(1,1,3,3-tetramethylbutyl)-6-benzotriazol-2-yl phenol]; transesterification product of 2-[3'-tert-butyl-5'-(2-methoxycarbonylethyl)-2'-hydroxyphenyl]-benzotriazole with polyethylene glycol 300; [R—CH$_2$CH$_2$—COO (CH$_2$)$_3$]$_2$— where R=3'-tert-butyl-4'-hydroxy-5'-2H-benzotriazol-2-yl phenyl.

2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

3. Esters of unsubstituted or substituted benzoic acids, for example 4-tert-butyl-phenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

4. Acrylates, for example ethyl and isooctyl α-cyano-β,β-diphenylacrylate, methyl α-carbomethoxycinnamate, methyl and butyl α-cyano-β-methyl-p-methoxycinnamate, methyl α-carbomethoxy-p-methoxycinnamate and N-(β-carbomethoxy-β-cyanovinyl)-2-methyl-indoline.

5. Sterically hindered amines, for example bis(2,2,6,6-tetramethylpiperidyl)sebacate, bis(2,2,6,6-tetramethylpiperidyl)succinate, bis(1,2,2,6,6-pentamethylpiperidyl)sebacate, bis(1,2,2,6,6-pentamethylpiperidyl)n-butyl-3,5-di-tert-butyl-4-hydroxybenzylmalonate, the product of the condensation of 1-hydroxyethyl-2,2,6,6-tetramethyl-4-hydroxypiperidine and succinic acid, the product of the condensation of N,N'-bis(2,2,6,6-tetramethyl-4-piperidyl) hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl) bis-(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)2-n-butyl-2-(2-hydroxy-3,5-di-tert-butylbenzyl)malonate, 3-n-octyl-7,7,9,9-tetramethyl-1,3,3-triazaspiro[4.5]decane-2,4-dione, bis(1-octyloxy-2,2,6,6-tetra-methylpiperidyl)sebacate, bis(1-octyloxy-2,2,6,6-tetramethylpiperidyl)succinate, the product of the condensation of N,N'-bis(2,2,6,6-tetramethyl-4-piperidyl) hexamethylene-diamine and 4-morpholino-2,6-dichloro-1,3,5-triazine, the product of the condensation of 2-chloro-4,6-di(4-n-butylamino-2,2,6,6-tetramethylpiperidyl)1,3,5-triazine and 1,2-bis(3-aminopropylamino) ethane, the product of the condensation of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9,-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, 2,4-bis[N-(1-cyclohexyloxy-2,2,6,6-tetramethylpiperidin-4-yl)-N-butylamino]-6-(2-hydroxyethyl)amino-1,3,5-triazine, the product of the condensation of 2,4-bis[1-cyclohexyloxy-2,2,6,6-tetramethylpiperidin-4-yl)butylamino]-6-chloro-s-triazine and N,N'-bis(3-aminopropyl)ethylenediamine.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and mixtures thereof with 2-ethoxy-2'-ethyl-5,4'-di-tert-butyloxanilide, and mixtures of o- and p-methoxy- and of o- and p-ethoxy-disubstituted oxanilides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,5-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxy-propytoxy)phenyl]-4,6-bis(2,4-dimethylphenyl)-1,3,5-triazine and 2-[4-dodecyl/tridecyloxy(2-hydroxypropyl)oxy-2-hydroxyphenyl]-4,6-bis(2,4-dimethylphenyl)-1,3,5-triazine.

8. Phosphites and phosphonites, for example triphenyl phosphite, diphenyl alkylphosphites, phenyl dialkylphosphites, tris(nonylphenyl)phosphite, trilauryl phosphite, trioctadecyl phosphite, distearyl pentaerythritol diphosphite, tris (2,4-di-tert-butylphenyl)phosphite, diisodecylpentaerythritol diphosphite, bis(2,4-di-tert-butylphenyl)pentaerythritol diphosphite, bis(2,6-di-tert-butyl-4-methylphenyl)pentaerythritol diphosphite, bisisodecyloxy-pentaerythritol diphosphite, bis(2,4-di-tert-butyl-6-methylphenyl)pentaerythritol diphosphite, bis(2,4,6-tri-tert-butylphenyl)pentaerythritol diphosphite, tristearylsorbitol triphosphite, tetrakis-(2,4-di-tert-butylphenyl)-4,4'-biphenylenediphosphonite, 6-isooctyloxy-2,4,8,10-tetra-tert-butyl-12H-dibenz[d,g]-1,3,2-dioxaphosphocine, 6-fluoro-2,4,8,10-tetra-tert-butyl-12-methyl-dibenz-[d,g]-1,3,2-dioxaphosphocine, bis(2,4-di-tert-butyl-6-methylphenyl) methylphosphite, and bis(2,4-di-tert-butyl-6-methylphenyl) ethylphosphite.

Examples of UV absorbers and light protection agents suitable as component (d) are also "Krypto-UVA", as are described, for example, in EP 180548. It is also possible to use latent UV absorbers, as described, for example, by Hida et al. in RadTech Asia 97, 1997, page 212.

It is also possible to use additives customary in the art, for example antistats, levelling auxiliaries and adhesion improvers.

To accelerate the photopolymerization it is possible to add, as further additives (d), a large number of amines, for example triethanolamine, N-methyldiethanolamine, ethyl p-dimethylaminobenzoate or Michlers ketone. The action of the amines can be intensified by the addition of aromatic ketones, e.g. of the benzophenone type. Examples of amines which can be used as oxygen scavengers are substituted N,N-dialkylanilines, as described in EP 339841. Other accelerators, coinitiators and autoxidators are thiols, thioethers, disulfides and phosphines, as described, for example, in EP 438123 and GB 2180358.

It is also possible to add chain transfer reagents customary in the art to the compositions according to the invention. Examples thereof are mercaptans, amines and benzothiazols.

The photopolymerization can also be accelerated by the addition of photosensitizers as further additives (d); these shift or broaden the spectral sensitivity. These are, in particular, aromatic carbonyl compounds, for example benzophenone, thioxanthone, in particular also isopropylthioxanthone, anthraquinone and 3-acylcoumarin derivatives, terphenyls, styryl ketones, and 3-(aroylmethylene)thiazolines, camphorquinone, but also eosin, rhodamine and erythrosine dyes.

As photosensitizers, it is also possible, for example, to consider the amines given above.

Further examples of such photosensitizers are

1. Thioxanthones thioxanthone, 2-isopropylthioxanthone, 2-chlorothioxanthone, 2-dodecylthioxanthone, 2,4-di-ethylthioxanthone, 2,4-dimethylthioxanthone, 1-methoxycarbonylthioxanthone, 2-ethoxy-carbonylthioxanthone, 3-(2-methoxyethoxycarbonyl)thioxanthone, 4-butoxycarbonylthioxanthone, 3-butoxycarbonyl-7-methylthioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfurylthioxanthone, 3,4-di-[2-(2-methoxyethoxy)ethoxycarbonyl]thioxanthone, 1-ethoxycarbonyl-3-(1-methyl-1-morpholinoethyl)thioxanthone, 2-methyl-6-dimethoxymethylthioxanthone, 2-methyl-6-(1,1-dimethoxybenzyl)thioxanthone, 2-morpholinomethylthioxanthone, 2-methyl-6-morpholinomethylthioxanthone, n-allylthioxanthone-3,4-dicarboximide, n-octylthioxanthone-3,4-dicarboximide, N-(1,1,3,3-tetra-methylbutyl)thioxanthone-3,4-dicarboximide, 1-phenoxythioxanthone, 6-ethoxycarbonyl-2-methoxythioxanthone, 6-ethoxycarbonyl-2-methylthioxanthone, thioxanthone-2-polyethylene glycol ester, 2-hydroxy-3-(3,4-dimethyl-9-oxo-9H-thioxanthon-2-yloxy)-N,N,N-trimethyl-1-propanaminium chloride;

2. Benzophenones benzophenone, 4-phenylbenzophenone, 4-methoxybenzophenone, 4,4'-dimethoxybenzophenone, 4,4'-dimethylbenzophenone, 4,4'-dichlorobenzophenone, 4,4'-dimethylaminobenzophenone, 4,4'-diethylaminobenzophenone, 4-methylbenzophenone, 2,4,6-trimethylbenzophenone, 4-(4-methylthiophenyl)benzophenone, 3,3'-dimethyl-4-methoxybenzophenone, methyl-2-benzoylbenzoate, 4-(2-hydroxyethylthio)benzophenone, 4-(4-tolylthio)benzophenone, 4-benzoyl-N,N,N-trimethylbenzenemethanaminium chloride, 2-hydroxy-3-(4-benzoylphenoxy)-N,N,N-trimethyl-1-propanaminium chloride monohydrate, 4-(13-acryloyl-1,4,7,10,13-pentaoxatridecyl)benzophenone, 4-benzoyl-N,N-dimethyl-N-[2-(1-oxo-2-propenyl)oxy]ethylbenzenemethanaminium chloride;

3. 3-Acylcoumarins 3-benzoylcoumarin, 3-benzoyl-7-methoxycoumarin, 3-benzoyl-5,7-di(propoxy)coumarin, 3-benzoyl-6,8-dichlorocoumarin, 3-benzoyl-6-chlorocoumarin, 3,3'-carbonylbis[5,7-di(propoxy)coumarin], 3,3'-carbonylbis(7-methoxycoumarin), 3,3'-carbonylbis(7-diethylaminocoumarin), 3-isobutyroylcoumarin, 3-benzoyl-5,7-dimethoxycoumarin, 3-benzoyl-5,7-diethoxycoumarin, 3-benzoyl-5,7-dibutoxycoumarin, 3-benzoyl-5,7-di(methoxyethoxy)coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 5,7-dimethoxy-3-(1-naphthoyl)coumarin, 5,7-dimethoxy-3-(1-naphthoyl)coumarin, 3-benzoylbenzo[f]coumarin, 7-diethylamino-3-thienoylcoumarin, 3-(4-cyanobenzoyl)-5,7-dimethoxycoumarin;

4. 3-(Aroylmethylene)thiazolines

3-Methyl-2-benzoylmethylene-β-naphthothiazoline, 3-methyl-2-benzoylmethylenebenzothiazoline, 3-ethyl-2-propionylmethylene-β-naphthothiazoline;

5. Anthracenes:

9,10-dimethoxy-anthracene, 9,10-diethoxy-anthracene, 9,10-dimethoxy-2-ethyl-anthracene, 6. Other Carbonyl Compounds Acetophenone, 3-methoxyacetophenone, 4-phenylacetophenone, benzil, 2-acetylnaphthalene, 2-naphthaldehyde, 9,10-anthraquinone, 9-fluorenone, dibenzosuberone, xanthone, 2,5-bis(4-diethylaminobenzylidene)cyclopentanone, α-(para-dimethylaminobenzylidene)ketones, such as 2-(4-dimethylaminobenzylidene)indan-1-one or 3-(4-dimethylaminophenyl)-1-indan-5-ylpropenone, 3-phenylthiophthalimide, N-methyl-3,5-di(ethylthio)phthalimide.

The curing process can also be aided, in particular, by pigmented compositions (e.g. with titanium dioxide), also by the addition as additional additive (d) of a component which forms the radicals under thermal conditions, for example an azo compound, such as 2,2'-azobis-(4-methoxy-2,4-dimethylvaleronitrile), a triazene, diazo sulfide, pentazadiene or a peroxy compound, for example hydroperoxide or peroxycarbonate, e.g. t-butyl hydroperoxide, as described, for example, in EP 245639.

As further additive (d), the compositions according to the invention can also comprise a photoreproducible dye, for example xanthene, benzoxanthene, benzothioxanthene, thiazine, pyronine, porphyrin or acridine dyes, or a radiation-cleavable trihalomethyl compound. Similar compositions are described, for example, in EP 445624.

Depending on the intended use, further customary additives (d) are optical brighteners, fillers, pigments, both white and coloured pigments, dyes, antistats, wetting agents or levelling auxiliaries.

For the curing of thick and pigmented coatings, the addition of microglass beads or pulverized glass fibres, as described, for example, in U.S. Pat. No. 5,013,768, is suitable.

The formulations can also comprise dyes or white or coloured pigments. Depending on the intended use, it is possible to use both inorganic and organic pigments. Such additives are known to the person skilled in the art, examples being titanium dioxide pigments, e.g. of the rutile or anatase type, carbon black, zinc oxide, such as zinc white, iron oxides, such as iron oxide yellow, iron oxide red, chromium yellow, chromium green, nickel, titanium yellow, ultramarine blue, cobalt blue, bismuth vanadate, cadmium yellow or cadmium red. Examples of organic pigments are mono- or bisazo pigments, and metal complexes thereof, phthalocyanine pigments, polycyclic pigments, for example perylene, anthraquinone, thioindigo, quinacridone or triphenylmethane pigments, and diketopyrrolopyrrole, isoindolinone, e.g. tetra-chloroisoindolinone, isoindoline, dioxazine, benzimidazolone and quinophthalone pigments.

The pigments can be used individually or else as mixtures in the formulations. Depending on the intended use, the pigments are added to the formulations in amounts customary in the art, for example in an amount of from 0.1 to 60% by weight, 0.1 to 30% by weight or 10 to 30% by weight, based on the total composition.

The formulations can, for example, also comprise organic dyes from very diverse classes. Examples are azo dyes, methine dyes, anthraquinone dyes or metal complex dyes. Customary concentrations are, for example, 0.1 to 20%, in particular 1 to 5%, based on the total compositions.

Depending on the formulation used, compounds can also neutralize the acids, in particular amines are used as stabilizers. Suitable systems are described, for example, in JP-A 11-199610. Examples are pyridine and derivatives thereof, N-alkylanilines or N,N-dialkylanilines, pyrazine derivatives, pyrrol derivatives, etc.

The choice of additives depends on the field of application in question and the properties desired for this field. The above-described additives (d) are customary in the art and are accordingly used in amounts customary in the art.

The invention also provides compositions comprising, as components (a), at least one ethylenically unsaturated photopolymerizable compound which is emulsified or dissolved in water.

Such radiation-curable aqueous prepolymer dispersions are available commercially in many variations. This is understood as meaning a dispersion of water and at least one prepolymer dispersed therein. The concentration of the water in these systems is, for example, 2 to 80% by weight, in particular 30 to 60% by weight. The radiation-curable prepolymers or prepolymer mixture is present, for example, in concentrations of from 95 to 20% by weight, in particular 70 to 40% by weight. In these compositions, the total of the percentages given for water and prepolymers is in each case 100, the auxiliaries and additives being added in varying amounts, depending on the intended use.

The radiation-curable film-forming prepolymers which are dispersed, and often also dissolved, in water are mono- or polyfunctional ethylenically unsaturated prepolymers which can be initiated by free radicals and are known per se for aqueous prepolymer dispersions, which have, for example, a content of from 0.01 to 1.0 mol per 100 g of prepolymer of polymerizable double bonds, and also an average molecular weight of, for example, at least 400, in particular from 500 to 10,000. However, depending on the intended use, prepolymers with higher molecular weights are also suitable.

Polyesters containing polymerizable C—C double bonds and having an acid number of at most 10, polyethers containing polymerizable C—C double bonds, hydroxyl-containing products of the reaction of a polyepoxide containing at least two epoxy groups per molecule with at least one α,β-ethylenically unsaturated carboxylic acid, polyurethane(meth)acrylates, and acrylic copolymers containing α,β-ethylenically unsaturated acrylic radicals, as are described in EP 12339. Mixtures of these prepolymers can likewise be used. Also suitable are the polymerizable prepolymers described in EP 33896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions based on specific (meth) acrylic alkyl ester polymers are described in EP 41125, and suitable water-dispersible, radiation-curable prepolymers of urethane acrylates can be found in DE 2936039.

As further additives, these radiation-curable aqueous prepolymer dispersions can also comprise the above-described additional additives (d), i.e., for example, dispersion auxiliaries, emulsifiers, antioxidants, light stabilizers, dyes, pigments, fillers, e.g. talc, gypsum, silica, rutile, carbon black, zinc oxide, iron oxides, reaction accelerators, levelling agents, lubricants, wetting agents, thickeners, matting agents, antifoams and other auxiliaries customary in surface coating technology. Suitable dispersion auxiliaries are water-soluble high molecular weight organic compounds having polar groups, for example polyvinyl alcohols, polyvinylpyrrolidone or cellulose ethers. Emulsifiers which may be used are nonionic, and, where appropriate, also ionic, emulsifiers.

The photoinitiators of the formula I according to the invention can also be dispersed as such in aqueous solutions and added in this dispersed form to the mixtures to be cured. Treated with suitable nonionic or, where appropriate, also ionic, emulsifiers, the compounds of the formula I according to the invention can be incorporated by mixing and e.g. binding into water. This produces stable emulsions which can be used as such as photoinitiators, in particular for aqueous photocurable mixtures as described above.

In certain cases, it may be advantageous to use mixtures of two or more of the photo-initiators according to the invention. It is of course also possible to use mixtures with known photoinitiators, e.g. mixtures with camphorquinone, benzophenone, benzophenone derivatives, acetophenone, acetophenone derivatives, for example α-hydroxycycloalkyl phenyl ketones or 2-hydroxy-2-methyl-1-phenylpropanone, dialkoxyacetophenones, α-hydroxy or α-aminoacetophenones, for example 4-methylthiobenzoyl-1-methyl-1-morpholinoethane, 4-morpholinobenzoyl-1-benzyl-1-dimethylaminopropane, 4-aroyl-1,3-dioxolanes, benzoin alkyl ethers and benzil ketals, for example benzil dimethyl ketal, phenyl glyoxalates and derivatives thereof, dimeric phenyl glyoxalates, peresters, e.g. benzophenonetetracarboxylic peresters, as described, for example, in EP 126541, monoacylphosphine oxides, for example (2,4,6-trimethylbenzoyl) phenylphosphine oxide, bisacylphosphine oxides, for example bis(2,6-dimethoxybenzoyl)(2,4,4-trimethylpent-1-yl)phosphine oxide, bis(2,4,6-trimethylbenzoyl)phenylphosphine oxide or bis(2,4,6-trimethylbenzoyl)(2,4-dipentoxyphenyl)phosphine oxide, trisacylphosphine oxides, halomethyltriazines, e.g. 2-[2-(4-methoxyphenyl)vinyl]-4,6-bistrichloromethyl-[1,3,5]triazine, 2-(4-methoxyphenyl)-4,6-bis-trichloromethyl-[1,3,5]triazine, 2-(3,4-dimethoxyphenyl)-4,6-bistrichloromethyl-[1,3,5]triazine, 2-methyl-4,6-bistrichloromethyl-[1,3,5]triazine, hexaarylbisimidazole/ coinitiator systems, e.g. ortho-chlorohexaphenylbisimidazole in combination with 2-mercaptobenzothiazole; ferrocenium compounds or titanocenes, for example dicyclopentadienylbis(2,6-difluoro-3-pyrrolophenyl)titanium. Coinitiators which may also be used are borate compounds.

In the case of the use of the photoinitiators according to the invention in hybrid systems, in this connection mixtures of free-radically and cationically curing systems are thus intended, in addition to the free-radical curing agents according to the invention, cationic photoinitiators, for example benzoyl peroxide (other suitable peroxides are described in U.S. Pat. No. 4,950,581, column 19, lines 17–25), aromatic sulfonium, phosphonium or iodonium salts, as described, for example in U.S. Pat. No. 4,950,581, column 18, line 60 to column 19, line 10, or cyclopentadienylareneiron(II) complex salts, e.g. ($\eta^6$-Isopropylbenzene)($\eta^5$-cyclopentadienyl)iron(II) hexafluorophosphate, are used.

The invention also provides compositions in which the additional photoinitiators (c) are compounds of the formula VIII, IX, X, XI, XII, XIII or mixtures thereof,

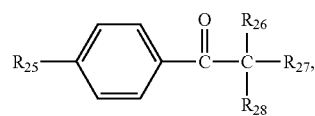
(VIII)

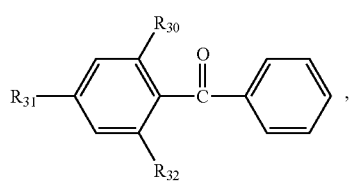
(IX)

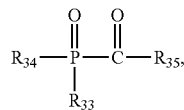
(X)

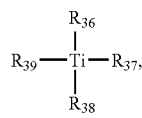
(XI)

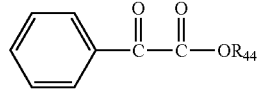
(XII)

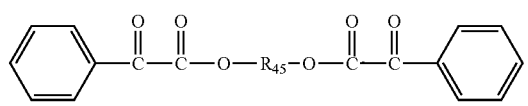
(XIII)

in which
$R_{25}$ is hydrogen, $C_1$–$C_{18}$alkyl, $C_1$–$C_{18}$alkoxy, —OCH$_2$CH$_2$—OR$_{29}$, morpholino, SCH$_3$, a group

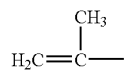

or a group

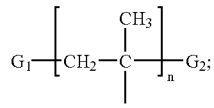

n has a value from 2 to 10;
$G_1$ and $G_2$ independently of one another are end-groups of the polymeric unit, in particular hydrogen or CH$_3$;
$R_{26}$ is hydroxyl, $C_1$–$C_{16}$alkoxy, morpholino, dimethylamino or —O(CH$_2$CH$_2$O)$_m$—C$_1$–C$_{16}$alkyl;
$R_{27}$ and $R_{28}$ independently of one another are hydrogen, $C_1$–$C_6$alkyl, phenyl, benzyl, $C_1$–$C_{16}$alkoxy or —O(CH$_2$CH$_2$O)$_m$—C$_1$–C$_{16}$alkyl, or $R_{27}$ and $R_{28}$ together with the carbon atom to which they are bonded form a cyclohexyl ring; where $R_{26}$, $R_{27}$ and $R_{28}$ are not all $C_1$–$C_{16}$alkoxy or —O(CH$_2$CH$_2$O)$_m$—C$_1$–C$_{16}$alkyl at the same time, and
m is a number from 1–20; and
$R_{29}$ is hydrogen,

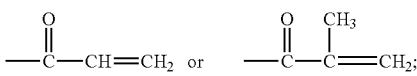

$R_{30}$ and $R_{32}$ independently of one another are hydrogen or methyl;
$R_{31}$ is hydrogen, methyl or phenylthio, where the phenyl ring of the phenylthio radical is unsubstituted or substituted by $C_1$–$C_4$alkyl in the 4-, 2-, 2,4- or 2,4,6-position;
$R_{33}$ and $R_{34}$ independently of one another are $C_1$–$C_{20}$alkyl, cyclohexyl, cyclopentyl, phenyl, naphthyl or biphenyl, where these radicals are unsubstituted or are substituted by halogen, $C_1$–$C_{12}$alkyl or $C_1$–$C_{12}$-alkoxy, or $R_{33}$ is an 8- or N-containing 5- or 6-membered heterocyclic ring, or are

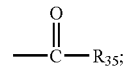

$R_{35}$ is cyclohexyl, cyclopentyl, phenyl, naphthyl or biphenyl, these radicals being unsubstituted or substituted by halogen, $C_1$–$C_4$alkyl or $C_1$–$C_4$alkoxy, or $R_{35}$ is an S— or N-containing 5- or 6-membered heterocyclic ring;
$R_{36}$ and $R_{37}$ independently of one another are unsubstituted cyclopentadienyl or cyclopentadienyl substituted once, twice or three times by $C_1$–$C_{18}$alkyl, $C_1$–$C_{18}$alkoxy, cyclopentyl, cyclohexyl or halogen; and
$R_{38}$ and $R_{39}$ independently of one another are phenyl which is substituted in at least one of the two ortho positions relative to the titanium-carbon bond by fluorine atoms or CF$_3$, and which on the aromatic ring may contain, as further substituents, unsubstituted pyrrolinyl or pyrrolinyl substituted by one or two $C_1$–$C_{12}$alkyl, di($C_1$–$C_{12}$alkyl)aminomethyl, morpholinomethyl, $C_2$–$C_4$alkenyl, methoxymethyl, ethoxymethyl, trimethylsilyl, formyl, methoxy or phenyl; or polyoxaalkyl, or
$R_{38}$ and $R_{39}$ are

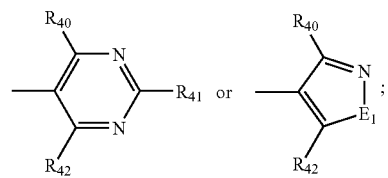

$R_{40}$, $R_{41}$ and $R_{42}$ independently of one another are hydrogen, halogen, $C_2$–$C_{12}$alkenyl, $C_1$–$C_{12}$alkoxy, $C_2$–$C_{12}$alkoxy interrupted by one to four O atoms, cycylohexyloxy, cyclopentyloxy, phenoxy, benzyloxy, unsubstituted phenyl or phenyl substituted by $C_1$–$C_4$alkoxy, halogen, phenylthio or $C_1$–$C_4$-alkylthio; or biphenyl, where $R_{40}$ and $R_{42}$ are not both hydrogen at the same time and in the radical

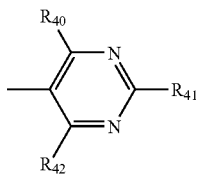

at least one radical $R_{40}$ or $R_{42}$ is $C_1$–$C_{12}$alkoxy, $C_2$–$C_{12}$alkoxy interrupted by one to four O atoms, cyclohexyloxy, cyclopentyloxy, phenoxy or benzyloxy;

$E_1$ is O, S or $NR_{43}$; and $R_{43}$ is $C_1$–$C_8$alkyl, phenyl or cyclohexyl, $R_{44}$ is H, $C_1$–$C_{12}$alkyl, $C_1$–$C_{12}$alkyl interrupted once or more than once by nonconsecutive O, $C_5$–$C_{10}$cycloalkyl, benzyl or phenyl;

$R_{45}$ is $C_1$–$C_{12}$alkylene, $C_4$–$C_8$-alkenylene, $C_4$–$C_8$alkynylene, cyclohexylene, $C_4$–$C_{40}$alkylene interrupted one or more times by —O—, —S— or —$NR_{46}$—, or is phenylene, or $R_{45}$ is a group selected from

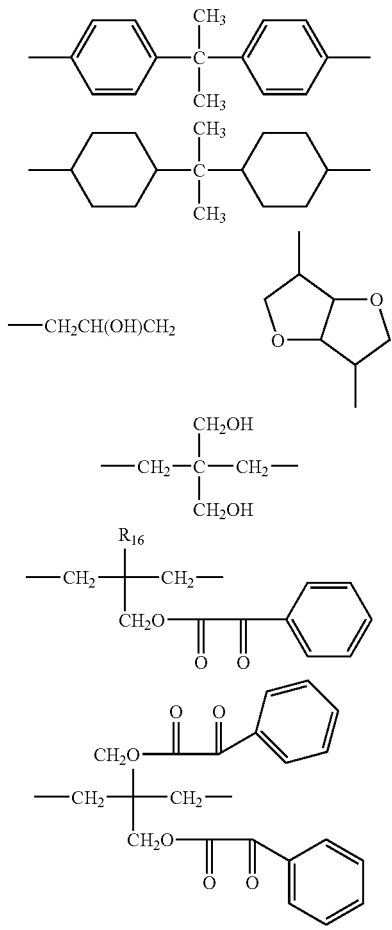

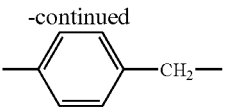

$R_{46}$ is hydrogen, $C_1$–$C_{12}$alkyl or phenyl.

$R_{25}$ as $C_1$–$C_{18}$alkyl can have the same meanings as described for the compounds of the formulae I, II or III. Also, $R_{27}$ and $R_{28}$ as $C_1$–$C_6$alkyl and $R_{26}$ as $C_1$–$C_4$alkyl can have the same meanings as described above apart from the respective number of carbon atoms.

$C_1$–$C_{18}$alkoxy is, for example, branched or unbranched alkoxy, for example methoxy, ethoxy, n-propoxy, isopropoxy, n-butoxy, isobutoxy, sec-butoxy, tert-butoxy, pentoxy, hexyloxy, heptyloxy, octyloxy, 2,4,4-trimethylpent-1-yloxy, 2-ethylhexyloxy, nonyloxy, decyloxy, dodecyloxy or octadecyloxy.

$C_2$–$C_{12}$alkoxy has the meanings given above apart from the corresponding number of carbon atoms.

$C_1$–$C_{16}$alkoxy has the same meanings as described above apart from the corresponding number of carbon atoms, and decyloxy, methoxy and ethoxy are preferred, in particular methoxy and ethoxy.

The radical —O($CH_2CH_2O$)$_m$—$C_1$–$C_{16}$alkyl stands for 1 to 20 consecutive ethylene oxide units whose chain ends with a $C_1$–$C_{16}$alkyl. Preferably, m is 1 to 10, e.g. 1 to 8, in particular 1 to 6.

Preferably, the ethylene oxide unit chain is terminated with a $C_1$–$C_{10}$alkyl, e.g. $C_1$–$C_8$alkyl, in particular with a $C_1$–$C_4$alkyl.

$R_{31}$ as a substituted phenylthio ring is, preferably, p-tolylthio.

$R_{33}$ and $R_{34}$ as $C_1$–$C_{20}$alkyl are linear or branched and are, for example, $C_1$–$C_{12}$alkyl, $C_1$–$C_8$alkyl, $C_1$–$C_6$alkyl or $C_1$–$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl, octadecyl, nonadecyl or icosyl. Preferably, $R_{33}$ as alkyl is $C_1$–$C_8$alkyl.

$R_{33}$, $R_{34}$ and $R_{35}$ as substituted phenyl are mono- to pentasubstituted, e.g. mono-, di- or trisubstituted, in particular tri- or disubstituted, on the phenyl ring. Substituted phenyl, naphthyl or biphenyl are substituted e.g. with a linear or branched $C_1$–$C_4$alkyl such as methyl, ethyl, n-propyl, isopropyl, n-butyl, isobutyl, s-butyl or t-butyl or with a linear or branched $C_1$–$C_4$alkoxy such as methoxy, ethoxy, n-propoxy, isopropoxy, n-butoxy, isobutoxy, s-butoxy or t-butoxy, preferably with methyl or methoxy.

If $R_{33}$, $R_{34}$ and $R_{35}$ are an S— or N-containing 5- or 6-membered heterocyclic ring, they are, for example, thienyl, pyrrolyl or pyridyl.

In the expression di($C_1$–$C_{12}$alkyl)aminomethyl, $C_1$–$C_{12}$alkyl has the same meanings as given above.

$C_2$–$C_{12}$alkenyl is linear or branched, can be mono- or polyunsaturated and is, for example, allyl, methallyl, 1,1-dimethylallyl, 1-butenyl, 2-butenyl, 1,3-pentadienyl, 1-hexenyl or 1-octenyl, in particular allyl.

$C_1$–$C_4$alkylthio is linear or branched and is, for example, methylthio, ethylthio, n-propylthio, isopropylthio, n-butylthio, isobutylthio, s-butylthio or t-butylthio, preferably methylthio.

$C_2$–$C_4$alkenyl is, for example, allyl, methallyl, 1-butenyl or 2-butenyl.

Halogen is fluorine, chlorine, bromine and iodine, preferably, fluorine, chlorine and bromine.

The term polyoxaalkyl includes $C_2$–$C_{20}$alkyl interrupted by 1 to 9 O atoms and stands, for example, for structural units such as $CH_3$—O—$CH_2$—, $CH_3CH_2$—O—$CH_2CH_2$—, $CH_3O[CH_2CH_2O]_y$—, where y=1–9, —$(CH_2CH_2O)_7CH_2CH_3$, —$CH_2$—$CH(CH_3)$—O—$CH_2$—$CH_2CH_3$.

Preference is given to compositions in which $R_{25}$ is hydrogen, —$OCH_2CH_2$—$OR_{29}$, morpholino, $SCH_3$, a group

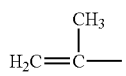

or a group

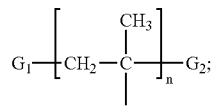

$R_{26}$ is hydroxyl, $C_1$–$C_{16}$alkoxy, morpholino or dimethylamino;

$R_{27}$ and $R_{28}$ independently of one another are $C_1$–$C_4$alkyl, phenyl, benzyl or $C_1$–$C_{16}$alkoxy, or $R_{27}$ and $R_{28}$ together with the carbon atom to which they are bonded form a cyclohexyl ring;

$R_{29}$ is hydrogen or

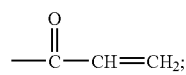

$R_{30}$, $R_{31}$, and $R_{32}$ are hydrogen;

$R_{33}$ is $C_1$–$C_{12}$alkyl, unsubstituted phenyl or phenyl substituted by $C_1$–$C_{12}$alkyl or $C_1$–$C_{12}$alkoxy;

$R_{34}$ is

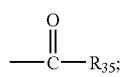

and $R_{35}$ is phenyl which is substituted by $C_1$–$C_4$alkyl or $C_1$–$C_4$alkoxy.

Preferred compounds of the formulae VIII, IX, X, XI, XII and XIII are α-hydroxycyclohexyl phenyl ketone or 2-hydroxy-2-methyl-1-phenylpropanone, (4-methylthiobenzoyl)-1-methyl-1-morpholinoethane, (4-morpholinobenzoyl)-1-benzyl-1-dimethylaminopropane, benzil dimethyl ketal, (2,4,6-trimethylbenzoyl)diphenylphosphine oxide, bis(2,6-dimethoxybenzoyl)-(2,4,4-trimethyl-pent-1-yl)phosphine oxide, bis(2,4,6-trimethylbenzoyl)phenylphosphine oxide or bis(2,4,6-trimethylbenzoyl)(2,4-dipentoxyphenyl) phosphine oxide and dicyclopentadienylbis(2,6-difluoro-3-pyrrolo)titanium, methyl-phenylglyoxalate.

Preference is also given to compositions in which, in the formula VIII $R_{27}$ and $R_{28}$ independently of one another are $C_1$–$C_6$alkyl, or together with the carbon atom to which they are bonded form a cyclohexyl ring, and $R_{26}$ is hydroxyl.

The proportion of compounds of the formula I (photoinitiator component (b)) in the mixture with compounds of the formulae VIII, IX, X or XI (=photoinitiator component (c)) is 5 to 99%, e.g. 20–80%, preferably 25 to 75%.

Also important are compositions in which, in the compounds of the formula VIII, $R_{27}$ and $R_{28}$ are identical and are methyl, and $R_{26}$ is hydroxyl or isopropoxy.

Likewise preferred are compositions comprising compounds of the formula I and compounds of the formula X in which $R_{33}$ is unsubstituted or mono- to tri-$C_1$–$C_{12}$alkyl- or $C_1$–$C_{12}$alkoxy-substituted phenyl or $C_1$–$C_{12}$alkyl;

$R_{34}$ is the group

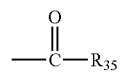

or phenyl; and $R_{35}$ is phenyl substituted by one to three $C_1$–$C_4$alkyl or $C_1$–$C_4$alkoxy.

Of particular interest are compositions as described above which comprise photoinitiator mixtures of the formulae I, VIII, IX, X, XI, XII or XIII and are liquid at room temperature. The preparation of the compounds of the formulae VIII, IX, X, XI, XII and XIII is generally known to the person skilled in the art and some of the compounds are available commercially. The preparation of oligomeric compounds of the formula VIII is described, for example, in EP 161463. A description of the preparation of compounds of the formula IX can, for example, be found in EP 209831. The preparation of compounds of the formula X is disclosed, for example, in EP 7508, EP 184095 and GB 2259704. The preparation of compounds of the formula XI is described, for example, in EP 318894, EP 318893 and EP 565488.

The photopolymerizable compositions advantageously comprise the photoinitiator in an amount of from 0.05 to 20% by weight, e.g. 0.05 to 15% by weight, preferably 0.1 to 5% by weight, based on the composition. The amount of photoinitiator stated is based on the total of all added photoinitiators if mixtures thereof are used, i.e. both on the photoinitiator (b) and on the photoinitiators (b)+(c).

Compounds according to the invention in which $Z_1$ or $Z_2$ are siloxane-containing radicals are particularly suitable as photoinitiators for surface coatings, in particular vehicle paints. These photoinitiators are not distributed as homogeneously as possible in the formulation to be cured, but enriched in a targeted manner on the surface of the coating to be cured, i.e. a targeted orientation of the initiator to the surface of the formulation takes place.

The photopolymerizable compositions can be used for various purposes, for example as printing inks, such as screen printing inks, flexographic printing inks or offset printing inks, as clearcoats, as colour coats, as white coats, e.g. for wood or metal, as powder coatings, as paints, inter alia for paper, water, metal or plastic, as daylight-curable coatings for marking buildings and roads, for photographic reproduction processes, for holographic recording materials, for image recording processes or for the production of printing plates which can be developed using organic solvents or aqueous-alkaline media, for the production of masks for screen printing, as dental filling materials, as adhesives, as pressure-sensitive adhesives, as laminating resins, as photoresists, e.g. galvanoresists, etch or permanent resists, both liquid and dry films, as photostructurable dielectrics, and as solder stopping masks for electronic circuits, as resists for the preparation of colour filters for any type of screen or for producing structures in the production process of plasma displays and electroluminescence displays, for the production of optical switches, optical gratings (interference gratings), for the preparation of three-dimensional objects by mass curing (UV curing in transparent moulds) or by the stereolithography process, as is described, for example, in U.S. Pat. No. 4,575,330, for the preparation of composite materials (e.g. styrenic polyesters which may contain glass fibres or other fibres and other auxiliaries) and other thick-layer materials, for the coating or sealing of electronic components or as coatings for optical fibres. The compositions are also suitable for the preparation of optical lenses, e.g. contact lenses and Fresnel lenses, and for the preparation of medical instruments, auxiliaries or implants.

The photoinitiators according to present invention are also suitable for use in compositions as coatings for optical fibers. In general, optical fibers are coated with protective coats directly after their production. The fiber of glass is drawn and then one or more coatings are applied to the glass string. Usually, one, two or three coats are applied, the top coating, for example, is colored ("ink layer or ink coating"). Further, several thus coated optical fibers may be put together to a bundle and be coated all together, i.e. cabling of the fibers. The compositions according to the present invention in general are suitable for any of these coatings, which have to exhibit good softness over a broad temperature range, good tensile strength and toughness and rapid UV-curing characteristics.

Each of the coats, inner primary (usually a soft coating), outer primary or secondary (usually a harder coating than the inner coating), tertiary or the cabling coat, may comprise at least one radiation-curable oligomer, at least one radiation curable monomer diluent, at least one photoinitiator, and additives.

In general all radiation curable oligomers are suitable. Preferred are oligomers with a molecular weight of at least 500, for example 500–10,000, 700–10,000, 1,000–8,000 or 1,000–7,000, in particular urethane oligomers, containing at least one unsaturated group. Preferably the radiation curable oligomer has two terminal functional groups. The coat may contain not only one specific oligomer, but also mixtures of different oligomers. The preparation of suitable oligomers is known to the person skilled in the art and for example published in U.S. Pat. No. 6,136,880, incorporated herein by reference. The oligomers are, for example, prepared by reacting an oligomer diol, preferably a diol having 2–10 polyoxaalkylene groups, with a diisocyanate or a polyisocyanate and a hydroxy-functional ethylenically unsaturated monomer, e.g. hydroxyalkyl(meth)acrylate. Specific examples of each of the components named above, as well as suitable ratios of these components are given in U.S. Pat. No. 6,136,880, incorporated herein by reference.

The radiation curable monomer can be used in a manner to control the viscosity of the coating formulation. Accordingly, a low viscosity monomer with at least one functional group capable of photoinitiated polymerization is employed. The amount for example is chosen to adjust the viscosity in a range from 1,000 to 10,000 mpas, i.e. usually for example from 10–90, or 10–80 wt % are used. The functional group of the monomer diluent preferably is of the same kind than the one of the oligomer component, for example an acrylate or vinyl ether function and a higher alkyl or polyether moiety. Examples of monomer diluents suitable for coating compositions for optical fibers are published in U.S. Pat. No. 6,136,880, col. 12, line 11 ff., incorporated herein by reference.

In primary coatings preferably monomers having an acrylate or vinyl ether functionality and a polyether moiety of 4 to 20 C atoms is used. Specific examples are given in the US patent incorporated by reference and cited above.

The composition may also comprise a poly(sitoxane) as described in U.S. Pat. No. 5,595,820 to improve the adhesive properties of the formulation on the optical fiber glass substrate.

The coating composition usually also comprises further additives, e.g. antioxidants, light stabilizers, UV absorbers such as for example given in the list above in particular $^{RTM}$IRGANOX 1035, 1010, 1076, 1222, $^{RTM}$TINUVIN P, 234, 320, 326, 327, 328, 329, 213, 292, 144, 622LD (all provided by Ciba Specialty Chemicals), $^{RTM}$ANTIGENE P, 3C, FR, GA-80, $^{RTM}$SUMISORB TM-061 (provided by Sumitomo Chemical Industries Co.), $^{RTM}$SEESORB 102, 103, 501, 202, 712, 704 (provided by Sypro Chemical Co., Ltd.), $^{RTM}$SANOL LS770 (provided by Sankyo Co. Ltd.) to prevent the coloring of the coat, in particular during the processing, and to improve the stability of the cured coat. Particularly interesting are stabilizer combinations of hindered piperidine derivatives (HALS) and hindered phenol compounds, e.g. a combination of IRGANOX 1035 and TINUVIN 292, for example in a ratio of 1:1. Further, additives are for example wetting agents and other additives having an effect on the rheology properties of the coating. Also amines, for example diethylamine, can be added.

Other examples for additives for compositions for the coating of optical fibers are silane coupling agents, e.g. γ-aminopropyltriethoxysilane, γ-mercaptopropyltrimethoxysilane, γ-methacryloxypropyl-trimethoxysilane, SH6062, SH6030 (provided by Toray-Dow Corning Silcone Co., Ltd.), KBE 903, KBE 603, KBE 403 (provided by Shin-Etsu Chemical Co., Ltd.)

In order to prevent coloring of the coatings the compositions may also comprise fluorescent additives or optical brighteners, as, for example, $^{RTM}$UVITEX OB, provided by Ciba Specialty Chemicals.

The photoinitiators according to the present application in coating compositions for optical fibers can be admixed with one or more other known photoinitiators. These are in particular monoacylphosphine oxides, such as diphenyl-2,4,6-trimethylbenzoyl phosphine oxide; bisacylphosphine oxides, such as bis(2,4,6-trimethylbenzoyl)-phenyl phosphine oxide ($^{RTM}$IRGACURE 819), bis(2,6-dimethoxybenzoyl)-2,4,4-trimethylpentyl phosphine oxide; α-hydroxyketones, such as 1-hydroxycyclohexyl phenyl ketone ($^{RTM}$IRGACURE 184), 2-hydroxy-2-methyl-1-phenyl-1-propanone ($^{RTM}$DAROCUR 1173), 2-hydroxy-1-[4-(2-hydroxy-ethoxy)phenyl]-2-methyl-1-propanone ($^{RTM}$IRGACURE 2959); α-aminoketones, such as 2-methyl-1-[4-(methylthio)phenyl]-2-(4-morpholinyl)-1-propanone ($^{RTM}$IRGACURE 907), 2-benzyl-2-(dimethylamino)-1-[4-(4-morpholinyl)phenyl]-1-butanone ($^{RTM}$IRGACURE 369); benzophenones, such as benzophenone, 2,4,6-trimethylbenzophenone, 4-methylbenzophenone, 2-methylbenzophenone, 2-methoxycarbonylbenzophenone, 4,4'-bis(chloromethyl)benzophenone, 4-chlorobenzophenone, 4-phenylbenzophenone, 4,4'-bis(dimethylamino)benzophenone, 4,4'-bis(diethylamino)benzophenone, methyl 2-benzoylbenzoate, 3,3'-dimethyl-4-methoxybenzophenone, 4-(4-methylphenylthio)benzophenone and also ketal compounds, for example 2,2-dimethoxy-1,2-diphenyl-ethanone ($^{RTM}$IRGACURE 651); monomeric or dimeric phenylglyoxalic acid esters, such as for example methyl phenylglyoxalic acid ester or 1,2-(benzoylcarboxy)ethane. In particular suitable are admixtures with mono- or bisacylphosphine oxides and/or α-hydroxy ketones.

It is evident that the formulations, in order to enhance the properties of the photoinitiators may also comprise sensitizer compounds, for example amines.

The coatings are either applied "wet on dry" or "wet on wet". In the first case after the application of the primary coat a curing step by irradiation with UV light is carried out prior to the application of the second coat. In the second case both coatings are applied and cured together by irradiation with UV light.

The curing with UV irradiation in this application usually takes place in a nitrogen atmosphere. In general all radiation sources usually employed in the photocuring technique can be used for the curing of optical fiber coatings. These are, for example the radiation sources listed below Generally, mercury medium pressure lamps or/and Fusion D lamps are used. Also flash lights are suitable. It is evident that the emission of the lamps is matched with the absorption of the photoinitiator or photoinitiator mixture which is used. The optical fiber coating compositions may also be cured by irradiation with an electron beam, in particular with low power electron beams, as is, for example disclosed in WO 98/41484.

In order to distinguish different fibers in an assembly, the fibers may be covered with a third colored coating ("ink coating"). The compositions used for this coating in addition to the polymerizable components and the photoinitiator comprise a pigment or dye. Examples for pigments suitable for optical fiber coatings are inorganic pigments, such as for example titanium dioxide, zinc oxide, zinc sulfide, barium sulfate, aluminium silicate, calcium silicate, carbon black, black iron oxide, copper chromite black, iron oxides, chromium oxide greens, iron blue, chrome green, violet (e.g. manganese violet, cobalt phosphate, $CoLiPO_4$), lead chromates, lead molybdates, cadmium titanate and pearlescent and metallic pigments, as well as organic pigments, such as monoazo pigments, di-azo pigments, di-azo condensation pigments, quinacridone pigments, dioxazine violet, vat pigments, perylene pigments, thiolndigo pigments, phthalocyanine pigments and tetrachloroisoindolinones. Examples for suitable pigments are carbon black for a black coating, titanium dioxide for a white coating, diarylide yellow or diazo based pigments for yellow coatings, phthalocyanine blue, and other phthalocyanines for blue coatings, anthraquinone red, naphthole red, monazo based pigments, quinacridone pigments, anthraquinone and perylenes for red coatings, phthalocyanine green and nitroso based pigments for green coatings, monazo and diazo based pigments, quinacridone pigments, anthraquinones and perylenes for orange coatings, and quinacridone violet, basic dye pigments and carbazole dioxazine based pigments for violet coatings. The person skilled in the art is well aware of formulating and combining suitable further pigments if even more colored coatings, such as aqua, brown, gray, pink etc. are needed. The mean particle size of the pigments usually is about 1 ☐m or less. The size of commercial pigments can be reduced by milling, if necessary. The pigments for example, can be added to the formulation in the form of a dispersion in order to simplify the mixing with the other ingredients of the formulation. The pigments are, for example dispersed in a low viscosity liquid, e.g. a reactive diluent. Preferred is the use of organic pigments. Suitable amounts for pigment in the ink coating are for example 1–20, 1–15, preferably 1–10 wt %. The ink coating in general also comprises a lubricant to provide improved break-out properties of the single coated optical fiber from the matrix. Examples of such lubricants are silicones, fluorocarbon oils or resins and the like, preferably a silicone oil or a functionalized silicone compound, e.g. silicone diacrylate is used.

The compositions according to the present invention are further suitable as a matrix material for an assembly of coated optical fibers. That is, several of the primary, secondary (and in some cases tertiary) coated fibers, for example, in the third coat being differentiated by different colors, are assembled in a matrix.

The coating of an assembly preferably besides the additives given above also contains a release agent to allow for easy access to the individual fibers during the installation of the optical fiber cables. i.e.

Examples for such release agents are teflon, silicones, silicon acrylates, fluorocarbon oils or resins and the like. The release agents suitably are added in an amount of 0.5–20 wt %. Examples of ink coatings and matrix materials for coated optical fibers are given in U.S. Pat. Nos. 6,197,422, 6,130, 980 and EP 614099, incorporated herein by reference.

The compositions are also suitable for the preparation of gels having thermotropic properties. Such gels are described, for example, in DE 19700064 and EP 678534.

Furthermore, the compositions can be used in dry-film paints, as are described, for example, in Paint & Coatings Industry, April 1997, 72 or Plastics World, Volume 54, No. 7, page 48(5).

The compounds according to the invention can also be used as initiators for emulsion, bead or suspension polymerizations or as initiators of a polymerization for the fixing of ordered states of liquid-crystalline mono- and oligomers, or as initiators for the fixing of dyes to organic materials.

In surface coatings, mixtures of a prepolymer with polyunsaturated monomers are often used which also contain a monounsaturated monomer. The prepolymer here is primarily responsible for the properties of the coating film, and variation thereof allows the person skilled in the art to influence the properties of the cured film. The polyunsaturated monomer functions as a crosslinking agent which renders the coating film insoluble. The monounsaturated monomer functions as a reactive diluent, by means of which the viscosity is reduced without the need to use a solvent.

Unsaturated polyester resins are mostly used in two-component systems together with a monounsaturated monomer, preferably with styrene. For photoresists, specific one-component systems are often used, for example polymaleimides, polychalcones or polyimides, as are described in DE 2308830.

The compounds according to the invention and mixtures thereof may also be used as free-radical photoinitiators or photoinitiating systems for radiation-curable powder coatings. The powder coatings may be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (e.g. methyl methacrylamide glycolate) and with a free-radical photoinitiator according to the invention, as described, for example, in the paper "Radiation Curing of Powder Coating", Conference Proceedings, Radtech Europe 1993 by M. Wittig and Th. Gohmann. Similarly, free-radically UV-curable powder coatings can be formulated by mixing unsaturated polyester resins with solid acrylates, methacrylates or vinyl ethers and with a photoinitiator (or photoinitiator mixture) according to the invention. The powder coatings can also comprise binders, as described, for example, in DE 4228514 and EP 636669. The UV-curable powder coatings can also comprise white or coloured pigments. Thus, for example, preferably rutile titanium dioxide may be used in concentrations of up to 50% by weight in order to obtain a cured powder coating with good coverage. The process normally involves electrostatic or tribostatic spraying of the powder onto the substrate, for example metal or wood, melting the powder by heating and, after a smooth film has formed, radiation-curing of the coating with ultraviolet or visible light, e.g. using medium-pressure mercury lamps, metal halide lamps or xenon lamps. A particular advantage of the radiation-curable powder coatings compared with their thermally curable counterparts is that the flow time after the melting of the powder particles can be extended as desired in order to ensure the formation of a smooth, high-gloss coating. In contrast to thermally curable systems, radiation-curable powder coatings can be formulated without the desired effect of a reduction in their service life such that they melt at relatively low temperatures. For this reason, they are also suitable as coatings for heat-sensitive substrates, for example wood or plastics.

In addition to the photoinitiators according to the invention, the powder coating formulations can also comprise UV absorbers. Appropriate examples have been listed above under points 1–8.

The photocurable compositions according to the invention are suitable, for example, as coating substances for substrates of all kinds, e.g. wood, textiles, paper, ceramic, glass, plastics such as polyesters, polyethylene terephthalate, polyolefins or cellulose acetate, in particular in the form of films, and also metals such as Al, Cu, Ni, Fe, Zn, Mg or Co and Ga, As, Si or $SiO_2$, on which a protective coating or, for example by imagewise exposure, an image is to be applied.

The substrates can be coated by applying a liquid composition, a solution or suspension to the substrate. The choice of solvent and the concentration depend primarily on the type of composition and on the coating procedure. The solvent should be inert, i.e. it should not undergo any chemical reaction with the components and should be capable of being removed again after the coating operation, in the drying process. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxy-ethanol, 2-ethoxyethanol, 1-methoxy-2-propanol, 1,2-dimethoxyethane, ethyl acetate, n-butyl acetate and ethyl 3-ethoxypropionate.

Using known coating processes, the formulation is applied to a substrate, e.g. by spincoating, dip coating, knife coating, curtain coating, brushing, spraying, especially, for example, by electrostatic spraying and reverse-roll coating, and by electrophoretic deposition. It is also possible to apply the photosensitive layer to a temporary, flexible support and then to coat the final substrate, e.g. a copper-laminated circuit board, by means of layer transfer via lamination.

The amount applied (layer thickness) and the type of substrate (layer support) are dependant on the desired field of application. The suitable layer thicknesses for the respective fields of application, e.g. in the photoresist field, printing ink field or paint field are known to the person skilled in the art. Depending on the field of application, the layer thickness range generally includes values from about 0.1 μm to more than 10 mm.

The radiation-sensitive compositions according to the invention are used, for example, as negative resists which have very high photosensitivity and can be developed in an aqueous-alkaline medium without swelling. They are suitable as photoresists for electronics, such as galvanoresists, etch resists, both in liquid and also dry films, solder stopping resists, as resists for the production of colour filters for any desired type of screen, or for the formation of structures in the manufacturing process of plasma displays and electroluminescence displays, for the production of printing plates, for example offset printing plates, for the production of printing formes for typographic printing, planographic printing, intaglio printing, flexographic printing or screen printing formes, the production of relief copies, e.g. for the production of texts in Braille, for the production of stamps, for use in moulding etching or use as microresists in the production of integrated circuits. The compositions may also be used as photostructurable dielectrics, for the encapsulation of materials or as insulator coating for the production of computer chips, printed circuits and other electrical or electronic components. The possible layer supports and the processing conditions of the coated substrates are varied accordingly.

The compounds according to the invention are also used for the production of single-layer or multilayer materials for image recording or image duplication (copies, reprography), which may be monotone or multicoloured. Furthermore, these materials can also be used as colour testing systems. In this technology, it is also possible to use formulations which contain microcapsules and, to generate the image, a thermal step can be connected downstream of the exposure step. Such systems and technologies and their applications are described, for example, in U.S. Pat. No. 5376459.

For photographic information recording, films made of polyester, cellulose acetate or plastic-coated papers, for example, are used, and for offset printing formes, specially treated aluminium, for example, is used, for the production of printed circuits, copper-faced laminates, for example, are used, and for the production of integrated circuits, silicon wafers are used. The usual layer thicknesses for photographic materials and offset printing forms are generally about 0.5 μm to 10 μm, and for printed circuits are from 1.0 μm to about 100 μm.

After the substrates have been coated, the solvent is usually removed by drying, to leave a layer of the photoresist on the support.

The term "imagewise" exposure encompasses both exposure via a photomask containing a predetermined pattern, for example a diapositive, exposure by a laser beam which is moved, for example under control by a computer, over the surface of the coated substrate, thereby generating an image, and irradiation with computer-controlled electron beams. It is also possible to use masks of liquid crystals which can be controlled pixel by pixel in order to generate digital images, as described, for example, by A. Bertsch, J. Y. Jezequel, J. C. Andre in Journal of Photochemistry and Photobiology A: Chemistry 1997, 107, p. 275–281 and by K.-P. Nicolay In Offset Printing 1997, 6, p. 34–37.

Conjugated polymers, for example polyanilines, can be converted from a semiconducting state to a conducting state by doping with protons. The photoinitiators according to the invention can also be used for the imagewise exposure of polymerizable compositions which contain such polymers in order to form conducting structures (in the irradiated zones) which are embedded in the insulating material (unexposed zones). Such materials can, for example, be used as wiring or connecting components for the production of electrical or electronic components.

Following the imagewise exposure of the material and prior to the developing, it may be advantageous to carry out a thermal treatment for a relatively short period. Here, only the exposed parts are thermally cured. The temperatures used are generally 50–150° C., preferably 80–130° C.; the thermal treatment time is usually between 0.25 and 10 minutes.

Furthermore, the photocurable composition can be used in a process for the production of printing formes or photoresists, as described, for example, in DE 4013358. Herein, prior to, simultaneously with or following the imagewise irradiation, the composition is briefly exposed to visible light having a wavelength of at least 400 nm without a mask. Following the exposure and the optional thermal treatment, the unexposed areas of the photoresist are removed using a developer in a manner known per se.

As already mentioned, the compositions according to the invention can be developed by aqueous-alkaline media. Suitable aqueous-alkaline developer solutions are, in particular, aqueous solutions of tetraalkylammonium hydroxides or of alkali metal silicates, phosphates, hydroxides and carbonates. Relatively small amounts of wetting agents or organic solvents can also be added to these solutions. Typical organic solvents which may be added to the developer liquids in small amounts are, for example, cyclohexanone, 2-ethoxyethanol, toluene, acetone and mixtures of such solutions.

Photocuring is of great importance for printing inks since the drying time of the binder is a crucial factor for the production rate of graphic products and should be in the order of magnitude of fractions of seconds. UV-curable inks are of importance particularly for screen, flexographic and offset printing.

As already mentioned, the mixtures according to the invention are also highly suitable for the production of printing plates. Here, mixtures of soluble linear polyamides or styrene/butadiene or styrene/isoprene rubber, polyacrylates or polymethyl methacrylates containing carboxyl groups, polyvinyl alcohols or urethane acrylates with photopolymerizable monomers, for example acryl- or methacrylamides or acrylic or methacrylic esters, and a photoinitiator, for example, are used. Films and plates made from these systems (wet or dry) are exposed via the negative (or positive) of the print original, and the uncured parts are subsequently washed out using a suitable solvent.

A further field of use for photocuring is the coating of metals, for example the coating of metal sheets and tubes, cans or bottlecaps, and the photocuring of plastic coatings, for example PVC-based floor or wall coverings. Examples of the photocuring of paper coatings are the colourless coating of labels, record sleeves or book covers.

Likewise of interest is the use of the compounds according to the invention for the curing of mouldings made from composite materials. The composite material consists of a self-supporting matrix material, e.g. a glass-fibre fabric, or else, for example, plant fibres [cf. K.-P. Mieck, T. Reussmann in Kunststoffe 85 (1995), 366–370], which is impregnated with the photocuring formulation. Mouldings made of composite materials produced using the compounds according to the invention have high mechanical stability and resistance. The compounds according to the invention can also be used as photocuring agents in moulding, impregnation or coating materials, as described, for example, in EP 7086. Such materials are, for example, fine coating resins, which are subject to strict requirements with regard to their curing activity and yellowing resistance, fibre-reinforced mouldings, for example planar or longitudinally or transversely corrugated light-diffusing panels. Processes for the production of such mouldings, for example hand lay-up techniques, fibre lay-up spraying, centrifugal or winding techniques, are described, for example, by P. H. Selden in "Glasfaserverstärkte Kunststoffe" [Glass-fibre-reinforced plastics], page 610, Springer Verlag Berlin-Heidelberg-New York 1967. Examples of articles which may be produced by this method are boats, chipboard or plywood panels coated on both sides with glass-fibre-reinforced plastic, pipes, sport articles, roof coverings, and containers etc. Further examples of moulding, impregnation and coating materials are UP resin fine coatings for mouldings containing glass fibres (GFP), e.g. corrugated sheets and paper laminates. Paper laminates may be based on urea or melamine resins. The fine coating is produced on a support (e.g. a film) prior to the production of the laminate. The photocurable compositions according to the invention can also be used for casting resins or for embedding articles, e.g. electronic components etc. Moreover, they can also be used for the lining of cavities and pipes. For curing, medium-pressure mercury lamps are used, as are customary in UV curing. However, less intensive lamps are also of particular interest, e.g. those of the type TL 40W/03 or TL40W/05. The intensity of these lamps corresponds approximately to that of sunlight. It is also possible to use direct sunlight for the curing. It is a further advantage that the composite material can be removed from the light source in a partially cured, plastic state and can be deformed. Curing is then carried out to completion.

The compositions and compounds according to the invention can also be used for the preparation of optical waveguides and optical switches, use being made of the generation of a difference in the refractive index between exposed and unexposed areas.

Also important is the use of photocurable compositions for imaging processes and for the optical production of information carriers. Here, as already described above, the coat (wet or dry) applied to the support is irradiated with UV or visible light via a photomask and the unexposed areas of the coat are removed by treatment with a solvent (=developer). The photocurable layer can also be applied to the metal by an electrodeposition technique. The exposed areas are crosslinked/polymeric and thus insoluble and remain on the support. Appropriate coloration produces visible images. If the support is a metallicized layer, then the metal can be removed from the unexposed areas by etching after exposure and developing, or can be strengthened by electroplating. Printed electronic circuits and photoresists can be produced in this way.

The photosensitivity of the compositions according to the invention generally ranges from 200 nm into the IR region, preferably 200 nm–600 nm. Suitable radiation comprises, for example, sunlight or light from artificial light sources. Therefore, a large number of very different types of light sources can be used. Point sources and flat radiators (lamp carpets) are suitable. Examples are: carbon arc lamps, xenon arc lamps, medium-pressure, high-pressure and low-pressure mercury lamps, optionally doped with metal halides (metal halogen lamps), microwave-stimulated metal vapour lamps, excimer lamps, superactinic fluorescent tubes, fluorescent lamps, incandescent argon lamps, flashlights, photographic floodlight lamps, light-emitting diodes (LED), electron beams and X-rays. The distance between the lamp and the substrate to be exposed according to the invention can vary depending on the intended use and lamp type and intensity, e.g. between 2 cm and 150 cm. Of particular suitability are laser light sources, e.g. excimer lasers, such as krypton F lasers for exposure at 248 nm. It is also possible to use lasers in the visible region. Using this method it is possible to produce printed circuits in the electronics industry, lithographic offset printing plates or relief printing plates, and also photographic image recording materials.

The invention therefore also provides a process for the photopolymerization of nonvolatile monomeric, oligomeric or polymeric compounds having at least one ethylenically unsaturated double bond, which comprises irradiating a composition as described above with light in the range from 200 nm into the IR region, preferably 200 nm–600 nm. The invention also provides for the use of the compounds of the formula I as photoinitiators for the photopolymerization of nonvolatile monomeric, oligomeric or polymeric compounds having at least one ethylenically unsaturated double bond by irradiation with light in the range from 200 nm into the IR region, preferably 200 nm–600 nm.

The invention also provides for the use of the above-described composition or a process for the preparation of pigmented and unpigmented surface coatings, coatings for optical fibres, glas fiber coating, printing inks, for example screen printing inks, offset printing inks, flexographic printing inks, powder coatings, printing plates, adhesives, dental compositions, optical waveguides, optical switches, colour testing systems, composite materials, glass fibre cable coatings, screen printing stencils, resist materials, colour filters, use for the encapsulation of electrical and electronic components, for the production of magnetic recording materials, for the production of three-dimensional objects using stereolithography, for photographic reproductions, and for use as image recording material, in particular for holographic recordings, for decolouring materials, for decolouring materials for image recording materials, for image recording materials using microcapsules.

The invention likewise provides a coated substrate which has been coated on at least one surface with a composition as described above, and also a process for the photographic production of relief images in which a coated substrate is subjected to imagewise exposure and then the unexposed portions are removed with a solvent. The imagewise exposure can be carried out via a mask or by means of a laser beam. Of particular interest here is exposure by means of a laser beam.

The examples below illustrate the invention in more detail, although it is not intended that the invention be limited to the examples. Unless stated otherwise, parts and percentages are based, as elsewhere in the description and in the claims, on the weight. Wherever reference is made to alkyl or alkoxy radicals having more than three carbon atoms without stating the isomer, then the n-isomers are always intended.

Preparation of the Starting Material

EXAMPLE 1a

Lithium (2,4,6-trimethylbenzoyl)phenylphosphine

Under argon and with the exclusion of moisture, 14.0 g of lithium (2.0 mol) are introduced into 250 ml of tetrahydrofuran at room temperature. Following the addition of 1.25 g of naphthalene, 44.8 g (0.25 mol) of dichlorophenylphosphine are added dropwise with stirring at 20–25° C. and, after stirring for 4 h, the black solution is filtered into a three-necked round flask through a frit (G2 porosity) with the exclusion of moisture and under argon as a protective gas. 47.2 g (0.258 mol) of 2,4,6-trimethylbenzoyl chloride are added dropwise at room temperature over the course of 30 minutes with stirring and cooling. Stirring for 2 hours gives the title compound as a red solution in tetrahydrofuran.
$^{31}$P-NMR δ 98.4 ppm.

EXAMPLE 1b

Preparation of lithium (2,4,6-trimethylbenzoyl)isobutylphosphine 34.4 ml (0.055 mol, +10%) of butyllithium 1.6M are slowly added dropwise, at 0° C.–10° C., to 4.5 g (0.025 mol) of isobutylphosphine (50% solution in toluene) in 30 ml of tetrahydrofuran. At the same temperature, 4.6 g (0.025 mol) of 2,4,6-trimethylbenzoyl chloride are then added dropwise. After warming to room temperature, the title compound is obtained as an orange suspension. The shift signal δ in the $^{31}$P-NMR spectrum appears at 50 ppm, measured against CDCl$_3$ as reference.

Preparation of the Compounds According to the Invention

EXAMPLE 2

Preparation of (Phenyl-{6-[phenyl-(2,4,6-trimethylbenzoyl)-phosphinoylmethyl]-pyridin-2-ylmethyl}-phosphinoyl)-(2,4,6-trimethyl-phenyl)-methanone

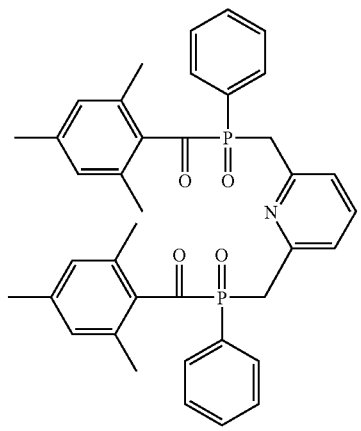

A compound of formula I wherein A is a group

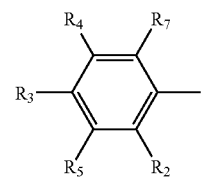

$R_1$, $R_2$ and $R_3$ are methyl, $R_4$ and $R_5$ are hydrogen,
R is phenyl,
W is a bond,
n is 2,
L is ethylene interrupted by pyridin-2-yl.

A solution of 1.32 g (0.005 mol) 2,6 bis(bromomethyl) pyridine in 5 ml tetrahydrofuran is added slowly at 20–30° C. to 12 ml (0.010 mol) lithium (2,4,6-trimethylbenzoyl) phenylphosphine. The reaction suspension is heated to 60° C. and, after the mixture has been afterstirred for 24 hours, it is concentrated using the Rotavap. The residue is taken up in 20 ml of toluene and is treated with 2.3 g (0.02 mol) of hydrogen peroxide 30%. After the mixture has been stirred for 2 hours between 20–30° C., the reaction is complete. The reaction emulsion is poured onto water and washed with aqueous saturated sodium hydrogencarbonate solution, then dried over magnesium sulfate and filtered. The filtrate is concentrated using the Rotavap. The residue is purified over silica gel and dried under a high vacuum. 0.4 g of the title compound are obtained as a yellow solid. Melting point: 192–193° C.

EXAMPLE 3

(Phenyl-{6-[phenyl-(2,4,6-trimethyl-benzoyl)-phosphinoyl]-hexyl}-phosphinoyl)-(2,4,6-trimethyl-phenyl)-methanone

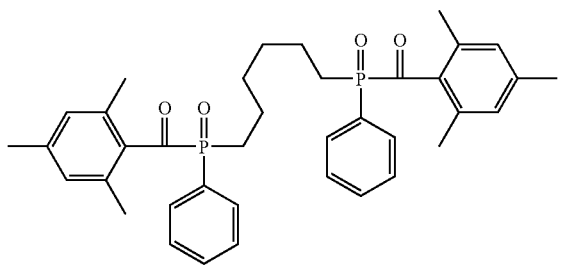

A compound of formula I wherein A is a group

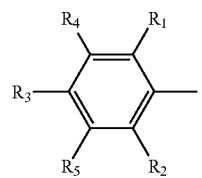

$R_1$, $R_2$ and $R_3$ are methyl, $R_4$ and $R_5$ are hydrogen,
R is phenyl,
W is a bond,
n is 2,
L is hexylene.

A solution of 1,22 g (0.005 mol) 1,6 dibromohexane in 5 ml tetrahydrofuran is added slowly at 20–30° C. to 12 ml (0.010 mol) lithium (2,4,6-trimethylbenzoyl)phenylphosphine. The reaction is carried out according to Example 2.

0.2 g of the title compound are obtained as a yellow solid. Melting point: 171–172° C.

EXAMPLE 4

(Phenyl-{2'-[phenyl-(2,4,6-trimethyl-benzoyl)-phosphinoylmethyl]-biphenyl-2-ylmethyl}-phosphinoyl)-(2,4,6-trimethyl-phenyl)-methanone

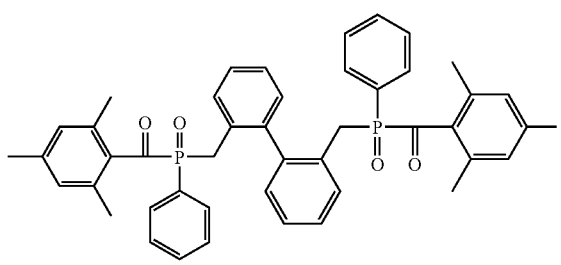

A compound of formula I wherein A is a group

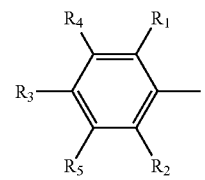

$R_1$, $R_2$ and $R_3$ are methyl, $R_4$ and $R_5$ are hydrogen,
R is phenyl,
W is a bond,
n is 2,
L is ethylene interrupted by biphenylene.

A solution of 1.70 g (0.005 mol)2,2' bis bromomethyl[1,1'] biphenyl in 5 ml tetrahydroturan is added slowly at 20–30° C. to 12 ml (0.010 mol) lithium (2,4,6-trimethyl-benzoyl)phenylphosphine. The reaction is carried out according to Example 2.

1.30 g of the title compound are obtained as a yellow solid. Melting point: 116–118° C.

EXAMPLE 5

({1-Methyl-4-[phenyl-(2,4,6-trimethyl-benzoyl)-phosphinoyl]-pentyl}-phenyl-phosphinoyl)-(2,4,6-trimethyl-phenyl)-methanone

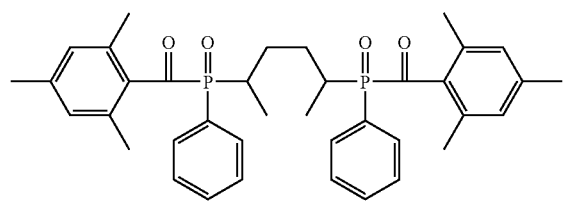

compound of formula I wherein A is a group

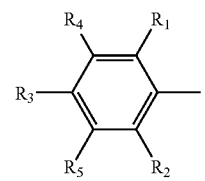

$R_1$, $R_2$ and $R_3$ are methyl, $R_4$ and $R_5$ are hydrogen,
R is phenyl,
W is a bond,
n is 2,
L is 2,5 hexylene.

A solution of 1.22 g (0.005 mol) 2,5 dibromohexane in 5 ml tetrahydrofuran is added slowly at 20–30° C. to 12 ml (0.010 mol) lithium (2,4,6-trimethylbenzoyl)phenylphosphine. The reaction is carried out according to Example 2.

0.10 g of the title compound are obtained as a yellow solid. Melting point: 167–169° C.

EXAMPLE 6

({3-Methyl-5-[phenyl-(2,4,6-trimethyl-benzoyl)-phosphinoyl]-pentyl}-phenyl-phosphinoyl)-(2,4,6-trimethyl-phenyl)-methanone

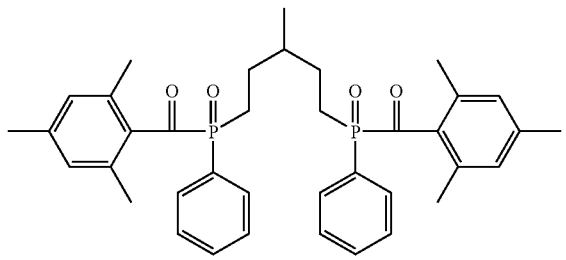

compound of formula I wherein A is a group

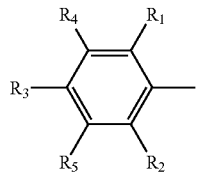

$R_1$, $R_2$ and $R_3$ are methyl, $R_4$ and $R_5$ are hydrogen,
R is phenyl,
W is a bond,
n is 2,
L is pentylene substituted by methyl.

A solution of 1.22 g (0.005 mol) 1,5 dibromo-3methyl pentane in 5 ml tetrahydrofuran is added slowly at 20–30° C. to 12 ml (0.010 mol) lithium (2,4,6-trimethylbenzoyl)phenylphosphine. The reaction is carried out acoording to Example 2.

0,10 g of the title compound are obtained as a yellow resin.

$^{31}$P-NMR (CDCl$_3$): 30.04 ppm
$^1$H-NMR (CDCl$_3$) : 7.76–7,70(m); 7.56–7.32(m); 6.59(s); 2.19–2.14(m); 1.99–1.92 (m); 0.89–0.87(m).

Application Example

A UV-curable white coating is prepared by mixing
67.5 parts of polyester acrylate oligomer ($^{RTM}$EBECRYL 830, UCB, Belgium)
5.0 parts of hexanediol diacrylate
2.5 parts of trimethylolpropane triacrylate
25.0 parts of rutile titanium dioxide ($^{RTM}$R-TC2, Tioxide, France)
2.0 parts of the photoinitiator from Example 2, 3 and 4.

The coating is applied to a coil-coated aluminium sheet using a 100 μm slotted doctor knife and then cured. Curing is carried out by conveying the sample 4–6 times, on a conveyor belt which is moving at a speed of 10 m/min, beneath an 80 W/cm medium-pressure mercury lamp (Hanovia, USA). The pendulum hardness is then determined in accordance with König (DIN53157) in [s]. The pendulum hardness is a measure of the through-curing of the composition. The higher the values, the more effective the curing which has been carried out. After the first pendulum hardness determination, the sample is after-exposed under low-pressure mercury lamps of the type TL 40W/03 (Philips; Emission maximum of 430 nm), and after 15 minutes and 16 hours the pendulum hardness is determined again. The final yellow index was determined in accordance with ASTMD 1925-88.

| Application Example | Initiator from Example | Number of passes at 10 m/min | Pendulum Hardness [s] after 15 min TL400W/03 | Pendulum Hardness [s] after 16 h TL400W/03 | Yellowness Index |
|---|---|---|---|---|---|
| 7 | 2 | 6 | 76 | 136 | 0.54 |
| 8 | 3 | 4 | 112 | 193 | 0.75 |
| 9 | 4 | 4 | 108 | 187 | 0.71 |

What is claimed is:
1. A compound of the formula I

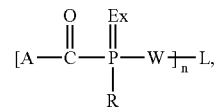

(I), in which
E is O or S and x is 0 or 1,
A is cyclopentyl, cyclohexyl, naphthyl, biphenylyl, anthracyl or an O-, S- or N-containing 5- or 6-membered heterocyclic ring, where the radicals cyclopentyl, cyclohexyl, naphthyl, biphenylyl, anthracyl or O-, S- or N-containing 5- or 6-membered heterocyclic ring are unsubstituted or substituted by halogen, $C_1$–$C_4$alkyl or $C_1$–$C_4$alkoxy; or
A is a group

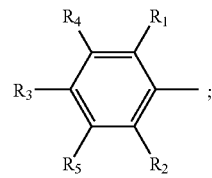

wherein
$R_1$ and $R_2$ independently of one another are $C_1$–$C_{24}$alkyl, OR$_{11}$, CF$_3$ or halogen;
$R_3$, $R_4$ and $R_5$ independently of one another are hydrogen, $C_1$–$C_{24}$alkyl, OR$_{11}$ or halogen; or
two of the radicals $R_1$, $R_2$, $R_3$, $R_4$ or $R_5$ together form $C_2$–$C_{12}$alkylene, which can be interrupted by O, S or NR$_{14}$;
R is $C_1$–$C_{24}$alkyl, unsubstituted or substituted by $C_3$–$C_{24}$cycloalkyl, $C_3$–$C_{24}$cycloalkenyl, phenyl, CN, C(O)R$_{11}$, C(O)OR$_{11}$, C(O)N(R$_{14}$)$_2$, OC(O)R$_{11}$, OC(O)OR$_{11}$, N(R$_{14}$)C(O)N(R$_{14}$), OC(O)NR$_{14}$, N(R$_{14}$)C(O)OR$_{11}$, halogen, OR$_{11}$, SR$_{11}$ or N(R$_{12}$)(R$_{13}$);
$C_2$–$C_{24}$alkyl which is interrupted once or more than once by nonconsecutive O, S or NR$_{14}$ and which is unsubstituted or substituted by phenyl, OR$_{11}$, SR$_{11}$, N(R$_{12}$)(R$_{13}$), CN, C(O)R$_{11}$, C(O)OR$_{11}$, or C(O)N(R$_{14}$)$_2$;
$C_2$–$C_{24}$alkenyl which is uninterrupted or interrupted once or more than once by nonconsecutive O, S or NR$_{14}$ and which is unsubstituted or substituted by OR$_{11}$, SR$_{11}$, N(R$_{12}$)(R$_{13}$), or $C_1$–$C_{12}$alkyl;

$C_5$–$C_{24}$cycloalkenyl which is uninterrupted or interrupted once or more than once by non-consecutive O, S or $NR_{14}$ and which is unsubstituted or substituted by $OR_{11}$, $SR_{11}$, $N(R_{12})(R_{13})$, or $C_1$–$C_{12}$alkyl;

$C_7$–$C_{24}$arylalkyl which is unsubstituted or substituted on the aryl group by $C_1$–$C_{12}$alkyl, $C_1$–$C_{12}$alkoxy or halogen;

$C_4$–$C_{24}$cycloalkyl which is uninterrupted or interrupted once or more than once by O, S or $NR_{14}$ and which is unsubstituted or substituted by $OR_{11}$, $SR_{11}$, $N(R_{12})(R_{13})$, or $C_1$–$C_{12}$alkyl;

$C_8$–$C_{24}$arylcycloalkyl or $C_8$–$C_{24}$arylcycloalkenyl; or;

R is a group of the formula

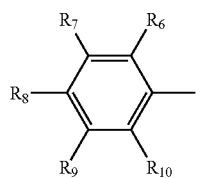

wherein $R_6$, $R_7$, $R_8$, $R_9$ and $R_{10}$ independently of one another are hydrogen, $C_1$–$C_{24}$alkyl; $C_2$–$C_{24}$alkyl which is interrupted once or more than once by nonconsecutive O, S or $NR_{14}$ and which is unsubstituted or substituted by OH, SH; $SR_{11}$ or $N(R_{12})(R_{13})$, $OR_{11}$, phenyl or halogen;

W is —CO—O— or —CO—N($R_{15}$)—;

L is a di-tri-or tetravalent linking group, n is a number of 2,3 or 4;

$R_{11}$ is hydrogen, $C_1$–$C_{20}$alkyl, $C_2$–$C_{20}$alkenyl, $C_3$–$C_8$cycloalkyl, phenyl unsubstituted or substituted by one or more $C_1$–$C_4$alkyl, benzyl or $C_2$–$C_{20}$alkyl which is interrupted once or more than once by O or S and which is unsubstituted or is substituted by OH or SH;

$R_{12}$ and $R_{13}$ independently of one another are hydrogen, $C_1$–$C_{20}$alkyl, $C_3$–$C_8$cycloalkyl, phenyl unsubstituted or substituted by one or more $C_1$–$C_4$alkyl, benzyl or $C_2$–$C_{20}$alkyl which is interrupted once or more than once by nonconsecutive O atoms and which is unsubstituted or substituted by OH or SH; or $R_{12}$ and $R_{13}$ together are $C_3$–$C_5$alkylene which is uninterrupted or interrupted by O, S or $NR_{14}$;

$R_{14}$ is hydrogen, phenyl unsubstituted or substituted by one or more $C_1$–$C_4$alkyl, $C_1$–$C_{12}$alkyl or $C_2$–$C_{12}$alkyl which is interrupted once or more than once by non-consecutive O or S atoms and which is unsubstituted or substituted by OH or SH;

$R_{15}$ is hydrogen, $C_1$–$C_{20}$alkyl, phenyl unsubstituted or substituted once or more with $C_1$–$C_4$alkyl.

2. A compound of the formula I according to claim 1 in which

A is a group

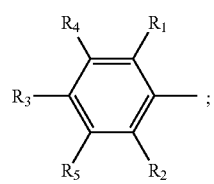

wherein

E is O or S and x is 0 or 1, $R_1$ and $R_2$ independently of one another are $C_1$–$C_{12}$alkyl, $OR_{11}$, $CF_3$ or halogen;

$R_3$, $R_4$ and $R_5$ independently of one another are hydrogen, $C_1$–$C_{12}$alkyl, $OR_{11}$ or halogen;

R is $C_1$–$C_{12}$alkyl, unsubstituted or substituted by phenyl, CN, $OR_{11}$, $C(O)R_{11}$, $C(O)OR_{11}$, $C(O)N(R_{14})_2$;

$C_2$–$C_{12}$alkyl which is interrupted once or more than once by nonconsecutive O and which is unsubstituted or substituted by phenyl, CN, $OR_{11}$, $C(O)R_{11}$, $C(O)OR_{11}$, $C(O)N(R_{14})_2$;

$C_2$–$C_{12}$alkenyl which is uninterrupted or interrupted once or more than once by nonconsecutive O and which is unsubstituted or substituted by $OR_{11}$, $N(R_{12})(R_{13})$, or $C_1$–$C_{12}$alkyl;

benzyl;

$C_4$–$C_8$cycloalkyl which is uninterrupted or interrupted once or more than once by O, S or $NR_{14}$ and which is unsubstituted or substituted by $OR_{11}$, $SR_{11}$, $N(R_{12})(R_{13})$, or $C_1$–$C_{12}$alkyl;

$C_8$–$C_{12}$arylcycloalkyl; or;

R is a group of the formula

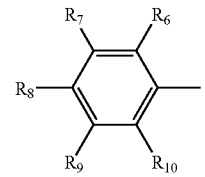

wherein $R_6$, $R_7$, $R_8$, $R_9$ and $R_{10}$ independently of one another are hydrogen, $C_1$–$C_{12}$alkyl; $OR_{11}$, phenyl or halogen;

W is —CO—O— or —CO—N($R_{15}$)—;

L is a di-or trivalent linking group, n is a number of 2 or 3;

$R_{11}$ is hydrogen, $C_1$–$C_{12}$alkyl, $C_5$–$C_6$cycloalkyl, phenyl or benzyl;

$R_{12}$ and $R_{13}$ independently of one another are hydrogen, $C_1$–$C_{12}$alkyl, phenyl, benzyl or $C_2$–$C_{12}$alkyl which is interrupted once or more than once by nonconsecutive O atoms and which is unsubstituted or substituted by OH or SH; or $R_{12}$ and $R_{13}$ together are piperidino, morpholino or piperazino;

$R_{14}$ is hydrogen, phenyl, $C_1$–$C_{12}$alkyl or $C_2$–$C_{12}$alkyl which is interrupted once or more than once by nonconsecutive O atoms and which is unsubstituted or substituted by OH or SH;

$R_{15}$ is hydrogen, $C_1$–$C_{12}$alkyl, phenyl unsubstituted or substituted once or more with $C_1$–$C_4$alkyl.

3. A process to prepare the compounds of formula I according to claim 1, by reacting compounds of formula II

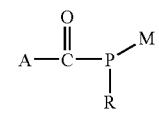

II wherein M is Li, Na or K, with a linking compound Hal-L-[Hal]$_m$ or Hal-W-L-[W-Hal]$_m$ wherein m is 1, 2 or 3 and oxidising the corresponding phosphines (x=0).

4. A photocurable composition comprising
(a) at least one ethylenically unsaturated photopolymerizable compound and
(b) at least one compound of the formula I according to claim 1 as photoinitiator.

5. A photocurable composition according to claim 4, comprising, in addition to components (a) and (b), further photoinitiators (c) or further additives (d).

6. A photocurable composition as claimed in claim 5, comprising, as further photoinitiator (c), at least one compound of the formula VIII, IX, X, XI, XII, XIII or mixtures thereof,

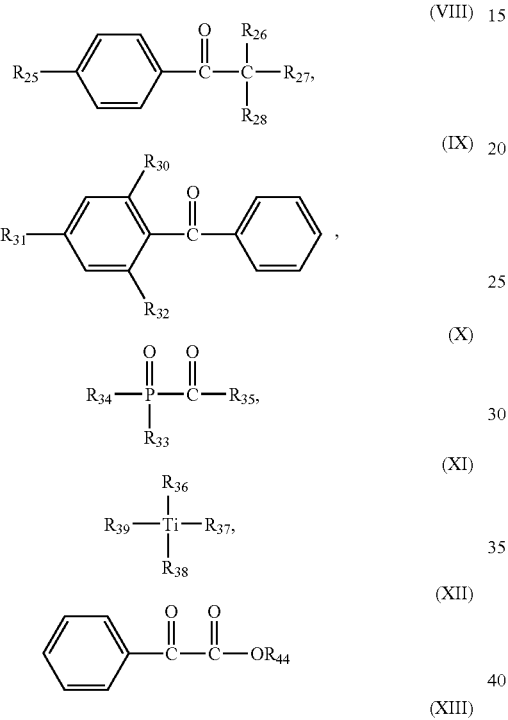

in which
$R_{25}$ is hydrogen, $C_1$–$C_{18}$alkyl, $C_1$–$C_{18}$alkoxy, —OCH$_2$CH$_2$—OR$_{29}$, morpholino, SCH$_3$, a group

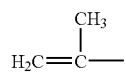

or a group

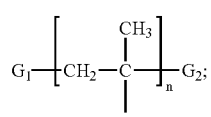

n has a value from 2 to 10;
$G_1$ and $G_2$ independently of one another are end-groups of the polymeric unit, in particular hydrogen or CH$_3$;

$R_{26}$ is hydroxyl, $C_1$–$C_{16}$alkoxy, morpholino, dimethylamino or —O(CH$_2$CH$_2$O)$_m$—C$_1$–C$_{16}$alkyl;

$R_{27}$ and $R_{28}$ independently of one another are hydrogen, $C_1$–$C_6$alkyl, phenyl, benzyl, $C_1$–$C_{16}$alkoxy or —O(CH$_2$CH$_2$O)$_m$—C$_1$–C$_{16}$alkyl, or $R_{27}$ and $R_{28}$ together with the carbon atom to which they are bonded form a cyclohexyl ring; where $R_{26}$, $R_{27}$ and $R_{28}$ are not all $C_1$–$C_{16}$alkoxy or —O(CH$_2$CH$_2$O)$_m$—C$_1$–C$_{16}$alkyl at the same time, and m is a number from 1–20; and $R_{29}$ is hydrogen,

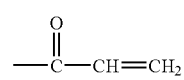

or

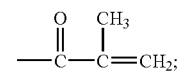

$R_{30}$ and $R_{32}$ independently of one another are hydrogen or methyl;

$R_{31}$ is hydrogen, methyl or phenylthio, where the phenyl ring of the phenylthio radical is unsubstituted or substituted by $C_1$–$C_4$alkyl in the 4-, 2-, 2,4- or 2,4,6- position;

$R_{33}$ and $R_{34}$ independently of one another are $C_1$–$C_{20}$alkyl, cyclohexyl, cyclopentyl, phenyl, naphthyl or biphenyl, where these radicals are unsubstituted or are substituted by halogen, $C_1$–$C_{12}$alkyl or $C_1$–$C_{12}$-alkoxy, or $R_{33}$ is an S- or N-containing 5- or 6-membered heterocyclic ring, or are

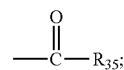

$R_{35}$ is cyclohexyl, cyclopentyl, phenyl, naphthyl or biphenyl, these radicals being unsubstituted or substituted by halogen, $C_1$–$C_4$alkyl or $C_1$–$C_4$alkoxy, or $R_{35}$ is an S— or N-containing 5- or 6-membered heterocyclic ring;

$R_{36}$ and $R_{37}$ independently of one another are unsubstituted cyclopentadienyl or cyclopentadienyl substituted once, twice or three times by $C_1$–$C_{18}$alkyl, $C_1$–$C_{18}$alkoxy, cyclopentyl, cyclohexyl or halogen; and $R_{38}$ and $R_{39}$ independently of one another are phenyl which is substituted in at least one of the two ortho positions relative to the titanium-carbon bond by fluorine atoms or CF$_3$, and which on the aromatic ring may contain, as further substituents, unsubstituted pyrrolinyl or pyrrolinyl substituted by one or two $C_1$–$C_{12}$alkyl, di($C_1$–$C_{12}$alkyl)aminomethyl, morpholinomethyl, $C_2$–$C_4$alkenyl, methoxymethyl, ethoxymethyl, trimethylsilyl, formyl, methoxy or phenyl; or polyoxaalkyl, or $R_{38}$ and $R_{39}$ are

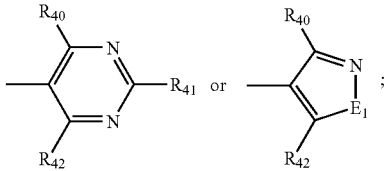

$R_{40}$, $R_{41}$, and $R_{42}$ independently of one another are hydrogen, halogen, $C_2$–$C_{12}$alkenyl, $C_1$–$C_{12}$alkoxy, $C_2$–$C_{12}$alkoxy interrupted by one to four O atoms, cyclohexyloxy, cyclopentyloxy, phenoxy, benzyloxy, unsubstituted phenyl or phenyl substituted by $C_1$–$C_4$alkoxy, halogen, phenylthio or $C_1$–$C_4$-alkylthio; or biphenyl, where $R_{40}$ and $R_{42}$ are not both hydrogen at the same time and in the radical

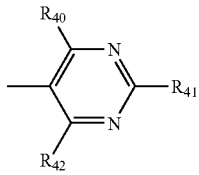

at least one radical $R_{40}$ or $R_{42}$ is $C_1$–$C_{12}$alkoxy, $C_2$–$C_{12}$alkoxy interrupted by one to four O atoms, cyclohexyloxy, cyclopentyloxy, phenoxy or benzyloxy;

$E_1$ is O, S or $NR_{43}$; and $R_{43}$ is $C_1$–$C_8$alkyl, phenyl or cyclohexyl, $R_{44}$ is H, $C_1$–$C_{12}$alkyl, $C_1$–$C_{12}$alkyl interrupted once or more than once by nonconsecutive O, $C_5$–$C_{10}$cycloalkyl, benzyl or phenyl;

$R_{45}$ is $C_1$–$C_{12}$alkylene, $C_4$–$C_8$-alkenylene, $C_4$–$C_8$alkynylene, cyclohexylene, $C_4$–$C_{40}$alkylene interrupted one or more times by —O—, —S— or —$NR_{46}$—, or is phenylene, or $R_{45}$ is a group selected from

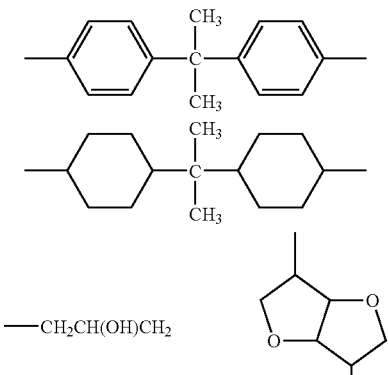

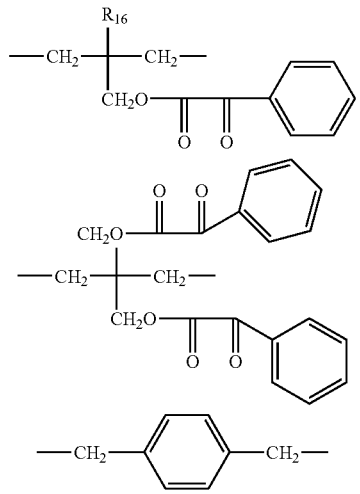

$R_{46}$ is hydrogen, $C_1$–$C_{12}$alkyl or phenyl.

7. A process for the photopolymerization of nonvolatile monomeric, oligomeric or polymeric compounds having at least one ethylenically unsaturated double bond, which comprises irradiating a composition according to claim 4 with light in the range from 200 nm into the IR region.

8. A coated substrate which has been coated on at least one surface with a composition according to claim 4.

9. A process to prepare the compounds of formula I'

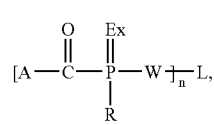

in which

E is O or S and x is 0 or 1,

A is cyclopentyl, cyclohexyl, naphthyl, biphenylyl, anthracyl or an O-, S- or N-containing 5- or 6-membered heterocyclic ring, where the radicals cyclopentyl, cyclohexyl, naphthyl, biphenylyl, anthracyl or O-, S- or N-containing 5- or 6-membered heterocyclic ring are unsubstituted or substituted by halogen, $C_1$–$C_4$alkyl or $C_1$–$C_4$alkoxy; or A is a group

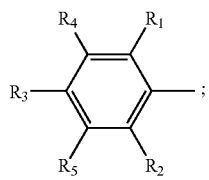

wherein $R_1$ and $R_2$ independently of one another are $C_1$–$C_{24}$alkyl, $OR_{11}$, $CF_3$ or halogen;

$R_3$, $R_4$ and $R_5$ independently of one another are hydrogen, $C_1$–$C_{24}$alkyl, $OR_{11}$ or halogen; or two of the radicals $R_1$, $R_2$, $R_3$, $R_4$ or $R_5$ together form $C_2$–$C_{12}$alkylene, which can be interrupted by O, S or $NR_{14}$;

R is a group of the formula

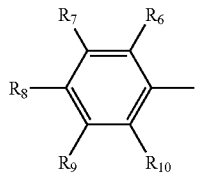

wherein $R_6, R_7, R_8, R_9$ and $R_{10}$ independently of one another are hydrogen, $C_1-C_{24}$alkyl; $C_2-C_{24}$alkyl which is interrupted once or more than once by nonconsecutive O, S or $NR_{14}$ and which is unsubstituted or substituted by OH, SH; $SR_{11}$ or $N(R_{12})(R_{13})$, $OR_{11}$, phenyl or halogen;

W is a bond,

L is a di-tri-or tetravalent linking group, n is a number of 2,3 or 4;

$R_{11}$ is hydrogen, $C_1-C_{20}$alkyl, $C_2-C_{20}$alkenyl, $C_3-C_8$cycloalkyl, phenyl unsubstituted or substituted by one or more $C_1-C_4$alkyl, benzyl or $C_2-C_{20}$alkyl which is interrupted once or more than once by O or S and which is unsubstituted or is substituted by OH or SH;

$R_{12}$ and $R_{13}$ independently of one another are hydrogen, $C_1-C_{20}$alkyl, $C_3-C_8$cycloalkyl, phenyl unsubstituted or substituted by one or more $C_1-C_4$alkyl, benzyl or $C_2-C_{20}$alkyl which is interrupted once or more than once by nonconsecutive O atoms and which is unsubstituted or substituted by OH or SH; or $R_{12}$ and $R_{13}$ together are $C_3-C_5$alkylene which is uninterrupted or interrupted by O, S or $NR_{14}$;

$R_{14}$ is hydrogen, phenyl unsubstituted or substituted by one or more $C_1-C_4$alkyl, $C_1-C_{12}$alkyl or $C_2-C_{12}$alkyl which is interrupted once or more than once by nonconsecutive O or S atoms and which is unsubstituted or substituted by OH or SH;

$R_{14}$ is hydrogen, phenyl unsubstituted or substituted by one or more $C_1-C_4$alkyl, $C_1-C_{12}$alkyl or $C_2-C_{12}$alkyl which is interrupted once or more than once by nonconsecutive O or S atoms and which is unsubstituted or substituted by OH or SH;

$R_{15}$ is hydrogen, $C_1-C_{20}$alkyl, phenyl unsubstituted or substituted once or more with $C_1-C_4$alkyl, by reacting compounds of formula II

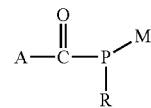

wherein M is Li, Na, K, with a linking compound Hal-L-[Hal]$_m$ or Hal-W-L-[W-Hal]$_m$ wherein m is 1, 2 or 3 and oxidising the corresponding phosphines (x=0).

* * * * *